US012662706B2

(12) United States Patent
Jain

(10) Patent No.: US 12,662,706 B2
(45) Date of Patent: Jun. 23, 2026

(54) CRENOLANIB FOR TREATING FLT3 MUTATED PROLIFERATIVE DISORDERS ASSOCIATED MUTATIONS

(71) Applicant: Arog Pharmaceuticals, Inc., Plano, TX (US)

(72) Inventor: Vinay K. Jain, Dallas, TX (US)

(73) Assignee: Arog Pharmaceuticals, Inc., Plano, TX (US)

( * ) Notice: Subject to any disclaimer, the term of this patent is extended or adjusted under 35 U.S.C. 154(b) by 1081 days.

(21) Appl. No.: 17/667,781

(22) Filed: Feb. 9, 2022

(65) Prior Publication Data

US 2022/0218694 A1 Jul. 14, 2022

Related U.S. Application Data

(63) Continuation-in-part of application No. 17/159,649, filed on Jan. 27, 2021, now abandoned, which is a continuation-in-part of application No. 15/799,684, filed on Oct. 31, 2017, now Pat. No. 11,078,541.

(60) Provisional application No. 62/416,475, filed on Nov. 2, 2016.

(51) Int. Cl.
*C12Q 1/6886* (2018.01)

(52) U.S. Cl.
CPC ..... *C12Q 1/6886* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,990,146 | A | 11/1999 | Boschelli et al. |
| 7,071,337 | B2 | 7/2006 | Kath et al. |
| 7,183,414 | B2 | 2/2007 | Tom et al. |
| 9,023,880 | B2 | 5/2015 | Jain |
| 9,101,624 | B2 | 8/2015 | Jain |
| 9,393,240 | B2 | 7/2016 | Jain |
| 9,480,683 | B2 | 11/2016 | Jain |
| 9,801,870 | B2 | 10/2017 | Jain |
| 11,078,541 | B2 | 8/2021 | Jain |
| 2004/0049032 | A1 | 3/2004 | Charrier et al. |
| 2005/0124599 | A1 | 6/2005 | Kath et al. |
| 2015/0031641 | A1 | 1/2015 | Levine et al. |
| 2015/0238479 | A1 | 8/2015 | Jain |

FOREIGN PATENT DOCUMENTS

| | | | |
|---|---|---|---|
| WO | 1999016755 | | 4/1999 |
| WO | 2001040217 | A1 | 6/2001 |
| WO | 2002032861 | A2 | 4/2002 |
| WO | 2002092599 | A1 | 4/2002 |
| WO | 2003024931 | | 3/2003 |
| WO | 2003024969 | | 3/2003 |
| WO | 2003035009 | | 5/2003 |
| WO | 2003037347 | | 5/2003 |
| WO | 2003057690 | | 7/2003 |
| WO | 2003099771 | | 12/2003 |
| WO | 2004005281 | A1 | 1/2004 |
| WO | 2004016597 | A2 | 2/2004 |
| WO | 2004018419 | A2 | 3/2004 |
| WO | 2004039782 | A1 | 5/2004 |
| WO | 2004043389 | A2 | 5/2004 |
| WO | 2004046120 | A2 | 6/2004 |

(Continued)

OTHER PUBLICATIONS

Garz et al Oncotarget. 8(65): 108738-108759 (Year: 2017).*
Wang et al Epigenetics. 18(1): 2139067 and Supplementary Table S1, 29 pages total (Year: 2023).*
Cortes et al Proc. ASCO, EHA Library, Abstract E919, Available via URL: <library.ehaweb.org/eha/2016/21st/132468/jorge.cortes.dose.escalation.study.of.crenolanib.in.combination.with.high.dose.html>, Abstract release date May 19, 2016 (Year: 2016).*
Wang et al Blood. 128(22):1071, Abstract 616 (Year: 2016).*
Fischer, et al. "Phase IIB trial of oral Midostaurin (PKC412), the FMS-like tyrosine kinase 3 receptor (FLT3) and multi-targeted kinase inhibitor, in patients with acute myeloid leukemia and high-risk myelodysplastic syndrome with either wild-type or mutated FLT3" J Clin Oncol, 2010. 28(28): p. 4339-45.

(Continued)

*Primary Examiner* — Carla J Myers
(74) *Attorney, Agent, or Firm* — Edwin S. Flores; Daniel J. Chalker; Chalker Flores, LLP

(57) ABSTRACT

The present invention includes methods for treating a human patient with Crenolanib, wherein the human patient is suffering from a FLT3 mutated leukemia, the method comprising: determining that the human patient has a poor prognosis by: obtaining or having obtained a leukemia biological sample and performing or having performed a genotyping assay on the biological sample to determine that the human patient has both a mutated FLT3 or a constitutively active FLT3 mutant and one or more driver mutations in one or more epigenetic regulator proteins that results in a loss of normal function of the epigenetic regulator proteins which, indicates that the patient has a poor prognosis; and administering to the patient determined to have the poor prognosis a therapeutically effective amount of Crenolanib, or a pharmaceutically acceptable salt thereof having the formula:

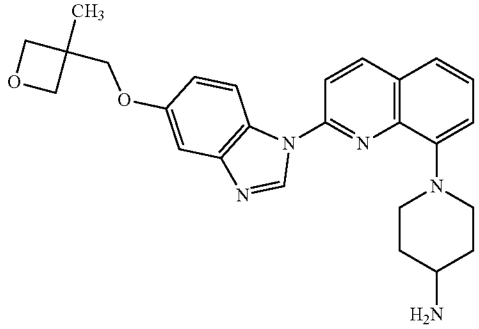

to treat the leukemia.

19 Claims, No Drawings

(56) References Cited

FOREIGN PATENT DOCUMENTS

| | | | |
|---|---|---|---|
| WO | 2004058749 | A1 | 7/2004 |
| WO | 2014107209 | A2 | 7/2014 |
| WO | 2018085292 | A1 | 5/2018 |

OTHER PUBLICATIONS

Fitchen, et al. "Genetically Engineered Protection Against Viruses in Transgenic Plants" (1993) Annu Rev. Microbiol. 47:739-764.
Galanis, et al. "Abstract 3660: Crenolanib: A next generation FLT3 Inhibitor" DOI: 10.1158/1538-7445AM2012-3660, Published Apr. 15, 2012, Cancer Research, vol. 72, Issue 8 Supplement, Abstract Only.
Gelsi-Boyer, et al. "Mutations in ASXL1 are associated with poor prognosis across the spectrum of malignant myeloid diseases" Mar. 2012, J Hematol Oncol, 5, 12. doi:10.1186/1756-8722-5-12.
Genecards, "GeneCards for DNMT3A" available via URL: genecards.org/cgi-bin/carddisp.plgene=DNMT3A , printed on Feb. 4, 2020, pp. 1-30 (Year: 2020).
Gilliland, et al. "The roles of FLT3 in hematopoiesis and leukemia." Blood. Sep. 1, 2002; 100: 1532-1542.
Greenblatt, et al. "Knock-in of a FLT3-ITD Mutation Cooperates with a NUP98-HOXD13 Fusion to Generate Acute Myeloid Leukemia in a Mouse model." Blood. vol. 119, No. 12, pp. 2883-2894 (Mar. 22, 2012).
Griswold, et al. "Effects of MLN518, a dual FLT3 and KIT inhibitor, on normal and malignant hematopoiesis" Blood. Nov. 2004; 104 (9): 2912-2918.
Astolfi, et al. (2019). "BCOR involvement in cancer" Epigenomics, 11(7), 835-855. doi:10.2217/epi-2018-0195.
Grunwald, et al. "FLT3 inhibitors for acute myeloid leukemia: a reviw for their efficacy and mechanisms of resistance" International Journal of Hematology, 2013.
Michmerhuizen, et al. "Mechanistic Insights and Potential Therapeutic Approaches for NUP98-Rearranged Hematologic Malignancies." Blood. vol. 136, No. 20, pp. 2275-2289 (Nov. 12, 2020).
Hattersley, et al. "What makes a good genetic association study" Genetic Epidemiology 5, Lancet, vol. 366, Oct. 8, 2005, 1315-1323.
Heidel, et al. "Clinical resistance to kinase inhibitor PKC412 in acute myeloid leukemia by mutation of Asn-676 in the FLY3 tyrosine kinase domian" Neoplasia, Jan. 1, 2006.
Herold, et al. "Isolated trisomy 13 defines a homogeneous AML subgroup with high frequency of mutations in spliceosome genes and poor prognosis," Blood. 2014;124:1304-1311.
Hirsch, et al. "Genetic hierarchy and temporal variegation in the clonal history of acute myeloid leukaemia" Nat Commun, 2016. 7: p. 12475.
Hirschorn, et al. "A Comprehensive Review of Genetic Association Studies" Mar./Apr. 2002, vol. =4, No. 2, 45-61.
Ho, et al. "Acquired Braf V600E Mutation as Resistant Mechanism after Treatment with Osimertinib" Journal of Thoracic Oncology, 2016.
Hocchaus, et al. "Molecular and and chromosomal mechanisms of resistance to Imatinib (STI571) therapy" Leukemia, 2002.
Hong, et al. "Src Mutation Induces Acquired Lapatinib Resistance in ERBB2-Amplified Human Gastroesophageal Adenocarcinoma Models" PLOS One, Oct. 2014.
Hou, et al. "Splicing Factor Mutations Predict Poor Prognosis in Patients with De Novo Acute Myeloid Leukemia." Oncotarget. vol. 7, No. 8, pp. 9084-9101 (Feb. 23, 2016).
Indian Patent Office, Examination Report for India Patent Appl. No. 201917020799, dated Sep. 30, 2021.
Japan Patent Office, Examination Report for Japan Patent Appl No. 2018-506309, dated Apr. 6, 2021, 6 pp.
Kaner, et al. "Acute Myeloid Leukemia (AML) with Somatic Mutations in PTPN11 Is Associated with Treatment Resistance and Poor Overall Survival" Nov. 29, 2018, Blood, 132(Supplement 1), 2760-2760. doi:10.1182/blood-2018-99-110319.
Katayama, et al. "Mechanisms of acquired crizotinib resistance in ALK-rearranged lung cancer" Science Translational Medicine, Feb. 2012.
Kelly, et al. (2019). "Bcor loss perturbs myeloid differentiation and promotes leukaemogenesis" Nat Commun, 10(1), 1347. doi:10.1038/s41467-019-09250-6.
Kindler, et al. "FLT3 as a therapeutic target in AML: still challenging after all these years" Blood. Dec. 9, 2010; 116:5089-102.
Kiyoi et al. "Prognostic implication of FLT3 and N-RAS gene mutations in acute myeloid leukemia" Blood. May 1, 1999; 93:3074-3080.
Kiyoi, et al. "Internal tandem duplication of FLT3 associated with leukocytosis in acute promyelocytic leukemia" Leukemia Study Group of the Ministry of Health and Welfare (Kohseisho). Leukemia. 1997; 11: 1447-1452.
Kiyoi, et al. "Internal tandem duplication of the FLT3 gene is a novel modality of elongation mutation which causes constitutive activation of the product" Leukemia. 1998; 12:1333-1337.
Klco, et al. "Functional heterogeneity of genetically defined subclones in acute myeloid leukemia" Cancer Cell, Mar. 17, 2014.
Korean Intellectual Property Office, International Search Report and Written Opinion for PCT/US2013/064821 dated Dec. 26, 2013, 5 pp.
Korean Intellectual Property Office, International Search Report and Written Opinion for PCT/US2017/059377 dated Oct. 31, 2017, 21 pp.
Kottaridis, et al. "The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Counsel AML 10 and 12 trials" Blood. Sep. 15, 2001; 98: 1742-1759.
Levis, et al. "A FLT3 tyrosine kinase inhibitor is selectively cytotoxic to acute myeloid leukemia blasts harboring FLT3 internal tandem duplication mutations" Blood. Aug. 1, 2001; 98(3): 885-887.
Levis, et al. "Small Moleucle FLT3 Tyrosine Kinase Inhibitors" Current Pharmaceutical Design. 2004, 10, 1183-1193.
Levis, et al. "Results from a randomized trial of salvage chemotherapy followed by lestaurtinib for patients with FLT3 mutant AML in first relapse," Blood. Mar. 24, 2011;117:3294-3301.
Lewis, et al. "Phase I Study of the Safety, Tolerability, and Pharmacokinetics of Oral CP-868,596, a Highly Specific Platelet-Derived Growth Factor Receptor Tyrosine Kinase Inhibitor in Patients With Advanced Cancers" J Clin Oncol. Nov. 1, 2009; 27(31) p. 5262-5269.
Michael, et al. "Phase Ib study of CP-868,596, a PDGFR inhibitor, combined with docetaxel with or without axitinib, a VEGFR inhibitor" British Journal of Cancer (published online Oct. 19, 2010) 103, 1554-1561.
Marcucci, et al. "Age-Related Prognostic Impact of Different Types of DNMT3A Mutations in Adults With Primary Cytogenetically Normal Acute Myeloid Leukemia" Journal of Clinical Oncology, vol. 30, No. 7, Mar. 1, 2012, 742-750.
Martin, et al. "Genomics in acute myeloid leukemia: from identification to personalization" Rhode Island Medical Journal, 2015, vol. 98, No. 11, pp. 27-30.
Martin, et al., "Genomics in actue myeloid luekemia: from identification to personalization", Rhode Island Medical Journal, Nov. 2015, vol. 98, No. 11, pp. 27-30.
McMahon, et al. "Clonal selection with Ras pathway activation mediates secondary clinical resistance to selective FLT3 inhibition in acute myeloid leukemia" Cancer Discov, 2019.
Mead, et al. "FLT3 tyrosine kinase domain mutations are biologically distinct from and have a significantly more favorable prognosis than FLT3 internal tandem duplications in patients with acute myeloid leukemia" Blood. Apr. 24, 2007; 110: 1262.
Mendler, et al., "RUNX1 mutations are associated with poor outcome in younger and older patients with cytogenetically normal acute myeloid leukemia and with distinct gene and MicroRNA expression signatures" J Clin Oncol, Sep. 1, 2012. 30(25): p. 3109-18.

(56) References Cited

OTHER PUBLICATIONS

Mendler, J., "RUNX1 Mutations Are Associated With Poor Outcome in Younger and Older Patients With Cytogenetically Normal Acute Myeloid Leukemia and With Distinct Gene and MicroRNA Expression Signatures," J. Clin. Oncol. vol. 30, No. 25, pp. 3109-3118 (Jul. 2, 2012).
Metzeler, et al. "Spectrum and prognostic relevance of driver gene mutations in acute myeloid leukemia" Blood, 2016. 128(5): p. 686-98.
Meyer, et al. "New insights to the MLL recombinome of acute leukemias" Apr. 2009, Leukemia, 23(8), 1490-1499. doi:10.1038/leu.2009.33.
Meyer, et al. "The MLL recombinome of acute leukemias in 2013" advance online publication, May 17, 2013, Leukemia, 27(11), 2165-2176. doi:10.1038/leu.2013.135.
Murata, et al., Selective cytotoxic mechanism of GTP-14564, a novel tyrosine kinase inhibitor in leukemia cells expressing a constitutively active Fms-like tyrosine kinase 3 (FLT3). J Biol Chem. Aug. 29, 2003; 278 (35): 32892-32898 [Epub Jun. 18, 2003].
Nakagawa, et al., "EGFR-TKI resistance due to BIM polymorphism can be circumvented in combination with HDAC inhibition" Cancer Res, Apr. 2013. 73(8): p. 2428-34.
Nakao, et al. "Internal tandem duplication of the FLT3 gene found in acute myeloid leukemia" Leukemia Dec. 10, 1996;10:1911-1918. (Abstract Only).
Nazarian, et al., "Melanomas acquire resistance to B-RAF(V600E) inhibition by RTK or N-RAS upregulation" Nature, Dec. 16, 2010. 468(7326): p. 973-7.
Nguyen, et al. "Myb expression is critical for myeloid leukemia development induced by Setbp1 activation" published online Nov. 16, 2016, Oncotarget, 7(52), 86300-86312. doi:10.18632/oncotarget.13383.
O Farrell, et al. "SU11248 is a novel FLT3 tyrosine kinase inhibitor with potent activity in vitro and in vivo" Blood, May 2003; 101(9): 3597-3605.
Odonnell, et al. "Acute myeloid leukemia" Journal of the National Comprehensive Cancer Network, 2011, vol. 9, No. 3, pp. 280-317.
Odonnell, et al., "Acute myeloid leukemia", Journal of the National Comprehensive Cancer Network, Mar. 2011, vol. 9, No. 3, pp. 280-317.
Papadimitrikopoulou, et al., "LBA51Analysis of resistance mechanisms to osimertinib in patients with T790M advanced NSCLC from the AURA3 study" Abstract Only, Annals of Oncology, 2018. 29(suppl_8).
Papaemmanuil, E., "Genomic Classification and Prognosis in Acute Myeloid Leukemia," New England J. Med. vol. 374, No. 23, pp. 2209-2221 (Jun. 9, 2016).
Papaemmanuil, et al. "Genomic Classification and Prognosis in Acute Myeloid Leukemia"—Supplemental Appendix, N Engl J Med, 2016. 374 (23): 275 pages.
Paschka, et al. "Wilms Tumor 1 Gene Mutations Independently Predict Poor Outcome in Adults With Cytogenetically Normal Acute Myeloid Leukemia: A Cancer and Leukemia Group B Study," J Clin Oncol. 2008;26:4595-4602. (Oct. 1, 2008).
Paschka, et al., "Wilms tumor 1 gene mutations independently predict poor outcome in adults with cytogenetically normal acute myeloid leukemia: a cancer and leukemia group B study" J Clin Oncol, Oct. 1, 2008. 26(28): p. 4595-602.
Patel, et al. "Prognostic Relevance of Integrated Genetic Profiling in Acute Myeloid Leukemia," New England J. Med. vol. 366, No. 12, pp. 1079-1189 (Mar. 22, 2012).
Patel, et al. "Prognostic relevance of integrated genetic profiling in acute myeloid leukemia" N Engl J Med, Mar. 22, 2012;366:1079-89.
Piazza, et al. "SETBP1 induces transcription of a network of development genes by acting as an epigenetic hub" Jun. 2018, Nat Commun, 9(1), 2192. doi:10.1038/s41467-018-04462-8.
Piccaluga, et al., "Imatinib mesylate in the treatment of hematologic malignancies" Expert Opin Biol Ther, 2007. 7 (10): p. 1597-611.
Podoltsev, et al. "Selecting initial treatment of acute myeloid leukaemia in older adults" Blood Reviews, 31, (2017) 46-62.
Pratcorona, et al., "Acquired Mutations in ASXL1 in Acute Myeloid Leukemia: Prevalence and Prognostic Value." Haematologica. vol. 97, No. 3, pp. 388-392 (Mar. 2012).
Quentmeier, et al., "BCR-ABL1-independent PI3Kinase activation causing imatinib-resistance" J Hematol Oncol, 2011. 4: p. 6.
Quivoron, et al. "TET2 inactivation results in pleiotropic hematopoietic abnormalities in mouse and is a recurrent event during human lymphomagenesis" Jul. 2011, Cancer Cell, 20(1), 25-38. doi:10.1016/j.ccr.2011.06.003.
Randhawa, et al. "Results of a Phase II Study of Crenolanib in Relapsed/Refractory Acute Myeloid Leukemia Patients (Pts) with Activating FLT3 Mutations" Blood, 2014. 124(21): p. 389-389.
Randhawa, et al. "Results of a Phase II Study of Crenolanib in Relapsed/Refractory Acute Myeloid Leukemia Patients with Activating FLT3 Mutations" Abstract Only, Blood, vol. 124, Issue 21 Blood Journal, Dec. 4, 2014, XP055570030.
Rasmussen, et al. "Role of TET enzymes in DNA methylation, development, and cancer" 2016, . Genes Dev, 30(7), 733-750. doi:10.1101/gad.276568.115.
Renneville, et al. "The Favorable Impact of CEBPA Mutations in Patients with Acute Myeloid Leukemia is Only Observed in the Absence of Associated Cytogenetic Abnormalities and FLT3 Internal Duplication." Blood. vol. 113, No. 21, pp. 5090-5093 (May 21, 2009).
Sasaki, et al. "IDH1(R132H) mutation increases murine haematopoietic progenitors and alters epigenetics" Aug. 2012, Nature, 488(7413), 656-659. doi:10.1038/nature11323.
Schnittger, et al. "Analysis of FLT3 length mutations in 1003 patients with acute myeloid leukemia: correlation to cytogenetics, FAB subtype, and prognosis in the AMLCG study and usefulness as a marker for the detection of minimal residual disease" Blood. 2002; 100: 59-66.
Sclenk, et al. "Mutations and Treatment Outcome in Cytogenetically Normal Acute Myeloid Leukemia" NEJM. May 1, 2008; 358: 1909.
Slany, et al. "The molecular Biology of Mixed Lineage Leukemia" Hematologica, 2009, 94(7) 984-993.
Small, Donald "FLT3 mutations: biology and treatment" Hematology Am Soc Hematol Educ Program. 2006: 178-84.
Smith, et al. "Single agent CEP-701, a novel FLT3 inhibitor, shows biologic and clinical activity in patients with relapsed or refractory acute myeloid leukemia" Blood, May 2004; 103: 3669-3676.
Smith, et al., "FLT3 D835 mutations confer differential resistance to type II FLT3 inhibitors" Leukemia, 2015. 29(12): p. 2390-2, accepted article preview online Jun. 25, 2015.
Smith, et al., "Validation of ITD mutations in FLT3 as a therapeutic target in human acute myeloid leukaemia" Nature, 2012. 485(7397): p. 260-3.
Sportoletti, et al. "Mouse Models of NPM1-mutated Acute Myeloid Leukemia: Biological and Clinical Implications." Leukemia. vol. 29, No. 2, pp. 269-278 (Feb. 2015).
Stirewalt, et al. "The role of FLT3 in haematopoietic malignancies" Nature Reviews Cancer. 2003; 3:650-665.
Stone, et al. "PKC-412 FLT3 inhibitor therapy in AML: results of a phase II trials" Ann Hematol. 2004; 83 Suppl 1: S89-90.
Stone, et al. "Patients with acute myeloid leukemia and an activating mutation in FLT3 respond to a small-molecule FLT3 tyrosine kinase inhibitor, PKC412" Jan. 2005, Blood, 105(1), 54-60. doi:10.1182/blood-2004-03-0891.
Sun, et al. "Epigenetic Regulators in the Development, Maintenance, and Therapeutic Targeting of Acute Myeloid Leukemia" Feb. 2018, Front Oncol, 8, 41. doi:10.3389/fonc.2018.00041.
Takahashi, Shinichiro "Downstream molecular pathways of FLT3 in the pathogenesis of acute myeloid leukemia biology and therapeutic implications" Journal of Hematology Oncology, 2011, 4:13.
Tao, et al. "Prognosis and Outcome of Patients with Acute Myeloid Leukemia Based on FLT3-ITD Mutations with or without Additional Abnormal Cytogenetics." Oncology Letters. vol. 18, No. 6, pp. 6766-6774 (Nov. 5, 2019).

(56) References Cited

OTHER PUBLICATIONS

Thanasopoulou, et al. "Potent Co-operation between the NUP98-NSD1 Fusion and the FLT3-ITD Mutation in Acute Myeloid Leukemia Induction." Haematologica. vol. 99, No. 9, pp. 1465-1471 (Jun. 22, 2014).
Thangavelu, et al. "Complete molecular risk stratification of de novo acute myeloid leukemia with intermediate cytogenetics using a nine-gene panel", Blood Journal, American Society of Hematology, 2014, vol. 124, No. 21, p. 2333.
Thiede, et al. "Analysis of FLT3-activating mutations in 979 patients with acute myelogenous leukemia: association with FAB subtypes and identification of subgroups with poor prognosis" Blood. 2002; 99:4326-4335.
Thol, et al. "SETBP1 mutation analysis in 944 patients with MDS and AML" E-pub May 7, 2013, Leukemia, 27(10), 2072-2075. doi:10.1038/leu.2013.145.
Tse, et al. "Inhibition of FLT3-mediated transformation by use of a tyrosine kinase inhibitor" Leukemia. Jul. 2001; 15 (7): 1001-1010.
Tyner, et al. "Functional genomic landscape of acute myeloid leukaemia" Nature, 2018.
ClinicalTrials.gov (NCT02283177) Last Update Posted Jul. 20, 2020, 11 pp.
Goldberg, et al. "Addition of Crenolanib to Induction Chemotherapy Overcomes the Poor Prognostic Impact of Co-Occurring Driver Mutations in Patients with Newly Diagnosed FL T3-Mutated AML" Blood (2018) 132 (Supplement 1) :1436.
Yang, et al. "Nuclear transport proteins: structure, function, and disease relevance" Signal Transduction and Targeted Therapy (2023) 8:425, published online Nov. 10, 2023.
Vanderwalde, A., "Genetics of Acute Myeloid Leukemia," available at http://emedicine.medscape.com/article/1936033-overview (last updated Apr. 1, 2016).
Venney, et al. "The Impact of Epigenetic Modifications in Myeloid Malignancies" May 2021, Int J Mol Sci, 22(9). doi:10.3390/ijms22095013.
Wagle, et al., "Dissecting Therapeutic Resistance to RAF Inhibition in Melanoma by Tumor Genomic Profiling" Journal of Clinical Oncology, Aug. 2011. 29(22): p. 3085-3096.
Wang, et al. "Safety Study of Crenolanib, a Type I FLT3 Inhibitor, with Cytarabine/Daunorubicin or Cytarabine/Idarubicin Induction and High-Does Cytarabine Consolidation in Newly Diagnosed FLT3+ AML" EHA Learning Center, Jun. 10, 2016; 133174 Abstract Only.
Weisberg, et al., "Drug resistance in mutant FLT3-positive AML" Oncogene, 2010. 29(37): p. 5120-34, published online Jul. 12, 2010.
Welsh et al: "Bioinformatics analysis to determine prognostic mutations of 72 de novo acute myeloid leukemia cases from the cancer genome atlas with 23 most common mutations and no abnormal cytogenetics", Annals of Clinical and Laboratory Science, 45(5), Jan. 1, 2015, pp. 515-521.
Welsh, et al. "Bioinformatics analysis to determine prognostic mutations of 72 de novo acute myeloid leukemia cases from the Cancer Genome Atlas (TCGA) with 23 most common mutations and no abnormal cytogentics" Annals of Clinical Laboratory Science, 2015, vol. 45, No. 5, pp. 515-521.
Winters, et al. "MLL-Rearranged Leukemias—An Update on Science and Clinical Approaches" Feb. 2017, Front Pediatr, 5, 4. doi:10.3389/fped.2017.00004.
Woyach, et al., "Resistance mechanisms for the Brutons tyrosine kinase inhibitor ibrutinib" N Engl J Med, Jun. 2014. 370(24): p. 2286-94.
Yamamoto, et al. "Activating mutation of D835 within the activation loop of FLT3 in human hematologic malignancies" Blood. Apr. 15, 2001;97:2434-2439.
Yee, et al. "SU5416 and SU5614 inhibit kinase activity of wild-type and mutant FLT3 receptor tyrosine kinase" Blood. Oct. 2002; 100(8): 2941-2949.
Yu, et al. "Clinical implications of recurrent gene mutations in acute myeloid leukemia" Dec. 2020, Experimental Hematology Oncology, 9(1), 4. doi:10.1186/s40164-020-00161-7.
Zhang, et al. "Association between increased mutation rates in DNMT3? and FLT3-ITD and poor prognosis of patients with acute myeloid leukemia" Experimental and Therapeutic Medicine, 2019.
Zhang, et al. "Clinical Resistance to Crenolanib in Acute Myeloid Leukemia Due to Diverse Molecular Mechanisms" Nature Communications, Jan. 2019, 10(1): 244, p. 1-13.
Zorko, et al. "Mll partial tandem duplication and Flt3 internal tandem duplication in a double knock-in mouse recapitulates features of counterpart human acute myeloid leukemias" 2012, Blood, 120(5), 1130-1136. doi:10.1182/blood-2012-03-415067.
Zorn, et al. "Crystal Structure of the FLT3 Kinase DomainBound to the Inhibitor Quizartinib (AC220)" PLOS One, Apr. 2, 2015.
Abdel-Wahab, et al. "ASXL1 mutations promote myeloid transformation through loss of PRC2-mediated gene repression" (Aug. 2012) Cancer Cell, 22(2), 180-193. doi:10.1016/j.ccr.2012.06.032.
Abu-Duhier, et al. "FLT3 internal tandem duplication mutations in adult acute myeloid leukemia define a high-risk group" British Journal of Hematology. Jun. 7, 2000; 111: 190-195.
Ahsan, et al. "Mechanism of Resistance to EGFR Tyrosine kinase Inhibitors and Therapeutic Approaches : An Update" Adv Exp Med Biol, 2016.
Al Aboud, et al. (2021). "Genetics, Epigentic Mechanism" In StatPearls [Internet]. Retrieved from https://www.ncbi.nlm.nih.gov/books/NBK532999/.
Amin, et al. "Having a higher blast percentage in circulation than bone marrow: clinical implications in myelodysplastic syndrome and acute lymphoid and myeloid leukemias" Leukemia. Jul. 28, 2005; 19: 1567-72.
Arber, et al. "The 2016 revision to the World Health Organization classification of myeloid neoplasms and acute leukemia" Blood, May 19, 2016. 127(20): p. 2391-405.
Arber, et al. "Initial Diagnostic Workup of Acute Leukemia: Guideline From the College of American Pathologists and the American Society of Hematology" Arch Pathol Lab Med, Oct. 2017. 141(10): p. 1342-1393.
Aslanyan, et al. "Clinical and Biological Impact of TET2 Mutations and Expression in Younger Adult AML Patients Treated within the EORTC/GIMEMA AML-12 Clinical Trial." Ann Hematol. vol. 93, No. 8, pp. 1401-1412 (Jul. 6, 2014).
Falini, et al. "NPM1-mutated acute myeloid leukemia: from bench to bedside." Blood. 136;15:1707-1721 (Oct. 8, 2020).
Bacher, et al. "Prognostic relevance of FLT3-TKD mutations in AML: the combination matters—an analysis of 3082 patients" Blood. Mar. 1, 2008; 111:2527-2537.
Badar, et al. Detectable FLT3-ITD or RAS mutation at the time of transformation from MDS to AML predicts for very poor outcomes. Leuk Res Dec. 2015;39:1367-74.
Bains, et al. "FLT3 and NPM1 mutations in myelodysplastic syndromes: Frequency and potential value for predicting progression to acute myeloid leukemia" American Journal of Clinical Pathology. Jan. 2011; 135: 62-69.
Bakshi, S., et al. "Trisomy 8 in leukemia: A GCRI experience," Indian J Hum Genet. 2012;18:106-108.
Ball, et al. "RAS Mutations are Independently Associated with Decreased Overall Survival and Event-free Survival in Patients with AML Receiving Induction Chemotherapy." Blood. vol. 134, No. Supp_1, pp. 18 (Nov. 13, 2019).
Banescu, et al. "The Value of FLT3, NPM1 and DNMT3A Gene Mutation Analysis in Acute Myeloid Leukemia Diagnosis" Revista Romana de Medicina de Laborator, 2019. 27(3): p. 239-243.
Belchis, et al. "Heterogeity of resistance mutations detectable by next-generation sequencing in TKI-treated lung adenocarcinoma" Oncotarget, vol. 7. No 29, Jun. 2016.
Bhamidpati, et al. FLT3 mutations in myelodysplastic syndromes (MDS) and chronic myelomonocytic leukemia (CMML). 2012. Journal of Clinical Oncology. Suppl; abstract 6597.
Bill, et al. "Mutational landscape and clinical outcome of patients with de novo acute myeloid leukemia and rearrangements involving 11q23/KMT2A" Oct. 2020, Proc Natl Acad Sci U S A, 117(42), 26340-26346. doi:10.1073/pnas.2014732117.
Bisio, et al. "NUP98-fusion Transcripts Characterize Different Biological Entities Within Acute Myeloid Leukemia." Leukemia. vol. 31, No. 4, pp. 974-977 (Apr. 2017).

(56) References Cited

OTHER PUBLICATIONS

Boddu, et al. "Influence of IDH on FLT3-ITD Status in Newly Diagnosed AML." Leukemia. vol. 31, No. 11, pp. 2526-2529 (Jul. 29, 2017).
Borthakur, et al. "Phase I study of sorafenib in patients with refractory or relapsed acute leukemias." Haematologica. Jan. 2011; 96: 62-8. Epub Oct. 15, 2010.
Cancer Genome Atlas Research, et al., "Genomic and epigenomic landscapes of adult de novo acute myeloid leukemia" with Supplemental Appendix (116 pages), N Engl J Med, May 30, 2013. 368(22): p. 2059-74.
Chabon, et al. "Circulating tumour DNA profiling reveals heterogeity of EGFR inhibitor resistance mechanisms in lung cancer patients" Nature Communications, Jun. 2016.
Chen, et al. (2021). "Lysine acetylation restricts mutant IDH2 activity to optimize transformation in AML cells" Mol Cell, 81(18), 3833-3847 e3811. doi:10.1016/j.molcel.2021.06.027.
Chen, et al. "Mutant and wild-type isocitrate dehydrogenase 1 share enhancing mechanisms involving distinct tyrosine kinase cascades in cancer" Published OnlineFirst on Mar. 12, 2019; Cancer Discov. doi:10.1158/2159-8290.CD-18-1040.
Cheson, et al. "Revised Recommendations of the International Working Group for Diagnosis, Standardization of Response Criteria, Treatment Outcomes, and Reporting Standards for Therapeutic Trials in Acute Myeloid Leukemia" J Clin Oncol. Dec. 15, 2003; 21: 4642-4649.
Chilton, et al. "The Prognostic Significance of Trisomy 4 in Acute Myeloid Leukaemia is Dependent on Age and Additional Abnormalities." Leukemia. vol. 30, No. 11, pp. 2264-2267 (Nov. 3, 2016).
Ching, et al. Abstract Only LB-215 "Analysis of mutations associated with response to glasdegib in acute myeloid leukemia (AML) and myelodysplastic syndrome (MDS)" Cancer Research, 2018.
Cho, et al. "Additional sex comb-like 1 (ASXL1), in cooperation with SRC-1, acts as a ligand-dependent coactivator for retinoic acid receptor" Jun. 2006, J Biol Chem, 281(26), 17588-17598. doi:10.1074/jbc.M512616200.
Choe, et al. "Molecular mechanisms mediating relapse following ivosidenib monotherapy in IDH1-mutant relapsed or refractory AML" May 12, 2020, Blood Adv, 4(9), 1894-1905. doi:10.1182/bloodadvances.2020001503.
ClinicalTrials.gov (NCT01522469), 3 pp.
ClinicalTrials.gov (NCT01657682).
ClinicalTrials.gov (NCT02283177).
ClinicalTrials.gov (NCT02400281).
ClinicalTrials.gov (NCT02626338).
Cortes, et al. "AC220, a potent, selective, second generation FLT3 receptor tyrosine kinase (RTK) inhibitor, in a first-in-human (FIH) phase I AML study" Blood (ASH Annual Meeting Abstracts) Nov. 2009.
Cortes, et al. "A phase II open-label, AC220 monotherapy efficacy study in patients with refractory/relapsed FLT3-ITD positive acute myeloid leukemia: updated interim results" Blood (ASH Annual Meeting Abstracts) Dec. 2011.
Cristobal, et al. "SETBP1 overexpression is a novel leukemogenic mechanism that predicts adverse outcome in elderly patients with acute myeloid leukemia" Jan. 2010, Blood, 115(3), 615-625. doi:10.1182/blood-2009-06-227363, Prepublished online as Blood First Edition paper, Nov. 16, 2009.
De Melo Galiato, et al. "Mechanisms of resistance and sensitivity to anti-HER2 therapies and anti-HER2 breast cancer" Oncotarget, vol. 7, No. 39. Jan. 2016.
Dicker, et al. "Trisomy 13 is strongly associated with AML1/RUNX1 mutations and increased FLT3 expression in acute myeloid leukemia," Blood. 2007;110:1308-1316.
DiNardo, et al. "Acute Myeloid Leukemia: from Mutation Profiling to Treatment Decisions" Curr Hematol Malig Rep, 2019.
Ding, et al. "Clonal evolution in relapsed acute myeloid leukaemia revealed by whole-genome sequencing" Nature, 2012. 481(7382): p. 506-10.
Dohner, et al. "Diagnosis and management of AML in adults: 2017 ELN recommendations from an international expert panel," Blood. vol. 129, No. 3, pp. 424-447 (Nov. 28, 2016).
Dohner, et al., "Diagnosis and management of AML in adults: 2017 ELN recommendations from an international expert panel" Blood, Jan. 26, 2017. 129(4): p. 424-447.
Drexler, et al. "Expression of FLT3 receptor and response to FLT3 ligand by leukemic cells" Leukemia. Apr. 10, 1996; 10:588-599 (Abstract Only).
Eckardt, et al. "Loss-of-Function Mutations of BCOR Are an Independent Marker of Adverse Outcomes in Intensively Treated Patients with Acute Myeloid Leukemia" 2021, Cancers (Basel), 13(9). doi:10.3390/cancers13092095.
Engleman, et al. "MET Amplification Leads Gefitinib Resistance in Lung by activating ERBB3 Signaling" Science, May 2007.
European Patent Office, European Search Report for EP Appl. No. 1786388.6 dated Apr. 25, 2019, 13 pp.
Ferrone, et al. "Age-Associated TET2 Mutations: Common Drivers of Myeloid Dysfunction, Cancer and Cardiovascular Disease" Jan. 17, 2020, Int J Mol Sci, 21(2). doi:10.3390/ijms21020626.

* cited by examiner

CRENOLANIB FOR TREATING FLT3 MUTATED PROLIFERATIVE DISORDERS ASSOCIATED MUTATIONS

CROSS-REFERENCE TO RELATED APPLICATIONS

This application is a continuation-in-part of U.S. patent application Ser. No. 17/159,649 filed Jan. 27, 2021, which is a continuation-in-part of U.S. patent application Ser. No. 15/799,684 filed on Oct. 31, 2017, now U.S. Pat. No. 11,078,541, which claims priority to U.S. Provisional Application Ser. No. 62/416,475, filed Nov. 2, 2016, the entire contents of which are incorporated herein by reference.

STATEMENT OF FEDERALLY FUNDED RESEARCH

Not applicable.

TECHNICAL FIELD OF THE INVENTION

The present invention relates in general to the use of Crenolanib in a pharmaceutically acceptable salt form for the treatment of proliferative disorder(s), characterized by mutations to particular tyrosine kinase pathways, and to a method of treatment of warm-blooded animals, preferably humans, in which a therapeutically effective dose of Crenolanib is administered to a subject suffering from said proliferative disorder.

INCORPORATION-BY-REFERENCE OF MATERIALS FILED ON COMPACT DISC

Not applicable.

BACKGROUND OF THE INVENTION

Without limiting the scope of the invention, its background is described in connection with protein kinases.

Protein kinases are enzymes that chemically modify other proteins by catalyzing the transfer of gamma phosphates from nucleotide triphosphates, often adenosine triphosphate (ATP), and covalently attaching them to a free hydroxyl group of amino acid residues serine, threonine and tyrosine.

Approximately 30% of all human proteins may be modified by kinase activity. Protein kinases direct the enzymatic activity, cellular location and primary function/association of substrate proteins and regulate cell signal transduction and cell function coordination.

Research studies have shown that aberrant expression of normal or mutated protein kinases are frequently associated with the formation and propagation of a number of diseases. Studies have shown that overexpression or inappropriate protein kinase expression is associated with cancer, cardiovascular disease, rheumatoid arthritis, diabetes, ocular disease, neurologic disorders and autoimmune disease.

The FMS-like tyrosine kinase 3 (FLT3) gene encodes a membrane-bound receptor tyrosine kinase that affects hematopoiesis leading to hematological disorders and malignancies. (Gilliland & Griffin, 2002; Stirewalt & Radich, 2003). Activation of FLT3 receptor tyrosine kinases is initiated through the binding of the FLT3 ligand (FLT3L) to the FLT3 receptor, also known as Stem cell tyrosine kinase-1 (STK-1) and fetal liver kinase-2 (flk-2), which is expressed on hematopoietic progenitor and stem cells.

FLT3 is one of the most frequently mutated genes in hematological malignancies, present in approximately 30% of adult acute myeloid leukemias (AML). (Kiyoi et al., 1998; Kottaridis et al., 2001) (Thiede et al., 2002; Yamamoto et al., 2001). FLT3 mutations have been detected in approximately 2% of patients diagnosed with intermediate and high risk myelodysplastic syndrome (MDS). (Bains, Luthra, Medeiros, & Zuo, 2011; Bhamidipati et al., 2012). Like MDS, the number of FLT3 mutations in patients with acute promyelocytic leukemia (APL) is small. The most common FLT3 mutations are internal tandem duplications (ITDs) that lead to in-frame insertions within the juxtamembrane domain of the FLT3 receptor. FLT3-ITD mutations have been reported in 15-35% of adult AML patients. (Kiyoi et al., 1997; Kiyoi et al., 1998; Schnittger et al., 2002). A FLT3-ITD mutation is an independent predictor of poor patient prognosis and is associated with increased relapse risk after standard chemotherapy, and decreased disease-free and overall survival. (Abu-Duhier et al., 2000; Kiyoi et al., 1999). Less frequent are FLT3 point mutations that arise in the activation loop of the FLT3 receptor. The most commonly affected codon is aspartate 835 (D835). Nucleotide substitutions of the D835 residue of the FLT3 receptor occur in approximately 5-10% of adult acute myeloid leukemia patients. (Bacher, Haferlach, Kern, Haferlach, & Schnittger, 2008; Stirewalt & Radich, 2003; Thiede et al., 2002; Yamamoto et al., 2001).

The heightened frequency of constitutively activated mutant FLT3 in adult AML has made the FLT3 gene a highly attractive drug target in this tumor type. Several FLT3 inhibitors with varying degrees of potency and selectivity for the target have been or are currently being investigated and examined in AML patients. (Kindler, Lipka, & Fischer, 2010).

FLT3 kinase inhibitors known in the art include Lestaurtinib (also known as CEP 701, formerly KT-555, Kyowa Hakko, licensed to Cephalon); CHIR-258 (Chiron Corp.); EB10 and IMC-EB10 (ImClone Systems Inc.); Midostaurin (also known as PKC412, Novartis AG); Tandutinib (also known as MLN-518, formerly CT53518, COR Therapeutics Inc., licensed to Millennium Pharmaceuticals Inc.); Sunitinib (also known as SU11248, Pfizer USA); Quizartinib (also known as AC220, Ambit Biosciences); XL 999 (Exelixis USA, licensed to Symphony Evolution, Inc.); GTP 14564 (Merck Biosciences UK); AG1295 and AG1296; CEP-5214 and CEP-7055 (Cephalon). The following PCT International Applications and U.S. patent applications disclose additional kinase modulators, including modulators of FLT3: WO 2002032861, WO 2002092599, WO 2003035009, WO 2003024931, WO 2003037347, WO 2003057690, WO 2003099771, WO 2004005281, WO 2004016597, WO 2004018419, WO 2004039782, WO 2004043389, WO 2004046120, WO 2004058749, WO 2004058749, WO 2003024969 and U.S. Patent Application Publication No. 2004/0049032. Known FLT3 kinase inhibitors have been tested in preclinical models as well as limited clinical trials. (Griswold et al., 2004; Levis et al., 2002; Levis & Small, 2004; Murata et al., 2003; O'Farrell et al., 2003; Smith et al., 2004; Stone et al., 2005; Tse, Novelli, Civin, Bohmer, & Small, 2001; Yee et al., 2002).

The aforementioned inhibitors have either been or are currently being investigated in the preclinical setting, or phase I and II trials as monotherapy in relapsed AML, or in phase III combination studies in relapsed AML. Despite reports of successful inhibition of FLT3 with these compounds in preclinical studies, complete remissions have rarely been achieved in FLT3 mutant AML patients in the clinical setting. For the majority of patients, the clinical response is short-lived. Response criteria for AML clinical trials are adapted from the International Working Group for AML. (Cheson et al., 2003). Responders are patients who obtain a Complete Response (CR), Complete Response with incomplete blood count recovery (CRi), or Partial Remission (PR). Briefly, criteria are as follows:

1. Complete Remission (CR):
   a. Peripheral blood counts:
      i. No circulating blasts
      ii. Neutrophil count >1.0×109/L
      iii. Platelet count >100×109/L
   b. Bone marrow aspirate and biopsy:
      i. <5% blasts
      ii. No Auer Rods
      iii. No extramedullary leukemia
2. Complete remission with incomplete blood count recovery (CRi):
   a. Peripheral blood counts:
      i. No circulating blasts
      ii. Neutrophil count <1.0×109/L, or
      iii. Platelet count <100×109/L
   b. Bone marrow aspirate and biopsy
      i. <5% blasts
      ii. No Auer Rods
      iii. No extramedullary leukemia
3. Partial remission:
   a. All CR criteria if abnormal before treatment except:
   b. >50% reduction in bone marrow blast but still >5%

To date, clinical responses to FLT3 inhibitors have been primarily limited to clearance of peripheral blood (PB) blasts, which frequently return within a matter of weeks, while bone marrow (BM) blasts remain largely unaffected. For example, treatment with sorafenib, a multi-kinase inhibitor with activity against mutant FLT3, while effective in clearing PB blasts, has resulted in only modest BM blast reductions. (Borthakur et al., 2011). BM blast percentage plays a central role in the diagnosis and classification of AML. The presence of a heightened percentage of blasts in BM is associated with significantly shorter overall survival. (Amin et al., 2005; Small, 2006). To effectively treat FLT3 mutated AML patients and overcome the significant unmet need in this patient population, an inhibitor is required that significantly depletes both PB and BM blasts, bridges high risk and heavily pretreated patients to stem cell transplant, and can help to decrease relapse rates and increase overall survival in early stage disease patients.

Independent of the patient's FLT3 status, genetic abnormalities—including recurrent mutations, chromosomal aneuploidies, and structural abnormalities—have historically played a critical role in characterizing leukemia, helping determine disease aggressiveness, response to treatment, and prognosis. In the following table, a "favorable risk" disease is associated with long-term survival of up to 65%, an "intermediate risk" disease is associated with long-term survival of about 25%, and an "adverse risk" disease is associated with long-term survival of less than 10%. (VanderWalde & Vora, 2016).

-continued

| Risk Group | Genetic Abnormality |
|---|---|
| Favorable Risk | t(8;21)(q22;q22.1); RUNX1-RUNX1T1<br>inv(16)(p13.1q22) or t(16;16)(p13.1;q22); CBFB-MYH11<br>Mutated NPM1 without FLT3-ITD or with FLT3-ITD$^{low}$<br>Biallelic mutated CEBPA |
| Intermediate Risk | Mutated NPM1 and FLT3-ITD$^{high}$<br>Wild-type NPM1 without FLT3-ITD or with FLT3-ITD$^{low}$ (without adverse-risk genetic lesions)<br>t(9;11)(p21.3;q23.3); MLLT3-KMT2A<br>Cytogenetic abnormalities not classified as favorable or adverse |
| Adverse Risk | t(6;9)(p23;q34.1); DEK-NUP214<br>t(v;11q23.3); KMT2A rearranged<br>t(9;22)(q34.1;q11.2); BCR-ABL1<br>inv(3)(q21.3q26.2) or t(3;3)(q21.3;q26.2); GATA2,MECOM(EVI1)<br>−5 or del(5q); −7; −17/abn(17p)<br>Complex karyotype, monosomal karyotype<br>Wild-type NPM1 and FLT3-ITD$^{high}$<br>Mutated RUNX1<br>Mutated ASXL1<br>Mutated TP53 |

Additionally, in the context of AML, clinicians and researchers have recently begun a progressive shift away from a morphologic classification scheme to one informed by causative genomic changes. (Papaemmanuil et al., 2016). Notably, a recent analysis of 1,540 AML patients revealed 5,234 "driver mutations" (using widely accepted genetic criteria for cancer-associated genes) involving 76 genes or regions within those patients, with mutation frequencies consistent with those found in previous studies. These driver mutations included recurrent fusion genes, aneuploidies, and leukemia gene mutations (such as base substitutions and small (200-bp) insertions or deletions), all found to display an effect on individual patient prognosis. At least one driver mutation was identified in 96% of patient samples, with two or more driver mutations found in 86% of patient samples. This comprehensive analysis led to the identification of previously unidentified leukemia-associated genes, as well as complex co-mutation patterns within these patient samples, indicating a renewed need to evaluate the prognoses of prospective AML patients in light of a renewed genomic classification scheme. Eleven genomic subgroups were proposed in light of this comprehensive study. Overall survival in these patient samples was correlated with the number of driver mutations, independent of age and cell count. Through a multivariate model designed to explore the relative contributions of genetic, clinical, and diagnostic variables to overall survival, genomic features were determined to be the most powerful predictor of overall patient survival. This study thus demonstrated considerable differences in clinical presentation and overall survival among the identified genomic subgroups. This finding, together with the discovery that the prognostic effects of individual mutations were significantly altered by the presence or absence of other driving mutations, suggests the necessity of assessing a number of driving mutations present in AML patients to provide a more comprehensive individual patient prognosis.

Consequently, the presence or absence of other driver lesions (including gene mutations, chromosomal aneuplodies, fusion genes, and complex karyotypes), has been demonstrated to provide a more comprehensive analysis of patient prognosis than the patient's status in one driver mutation alone.

In light of this background, the need for the development of therapies capable of overcoming these particularly grim patient prognoses takes on a renewed importance. The current invention seeks to overcome the many disadvantages of the prior art.

SUMMARY OF THE INVENTION

As embodied and broadly described herein, an aspect of the present disclosure relates to a method for treating a human patient with Crenolanib, wherein the human patient is suffering from a FLT3 mutated leukemia, the method comprising: determining that the human patient has a poor prognosis for the FLT3 mutated leukemia by: obtaining or having obtained a leukemia biological sample from the human patient; and performing or having performed a genotyping assay on the biological sample to determine that the human patient has both a mutated FLT3 or a constitutively active FLT3 mutant and one or more driver mutations in one or more epigenetic regulator proteins that results in a loss of normal function of the one or more epigenetic regulator proteins, wherein the presence of both the mutated FLT3 and the one or more driver mutations in the one or more epigenetic regulator proteins indicates that the patient has a poor prognosis; and administering to the patient determined to have the poor prognosis a therapeutically effective amount of Crenolanib or a pharmaceutically acceptable salt thereof, to treat the leukemia. In one aspect, the FLT3 mutation is selected from at least one of FLT3-ITD or FLT3-TKD. In another aspect, the epigenetic regulator protein is at least one of TET2, IDH1, IDH2, ASXL1, BCOR, SETBP1, or MLL. In another aspect, the driver mutation in TET2 is a loss-of-function mutation. In another aspect, the driver mutation the loss-of-function mutation in TET2 is selected from at least one of a frameshift mutation, a nonsense mutation, or a missense mutation at amino acid residues between D1129 and G1936 inclusive in the catalytic domain. In another aspect, the driver mutation in IDH1 is selected from at least one of a missense mutation at amino acid residue R132. In another aspect, the driver mutation in IDH2 is selected from at least one of a missense mutation at amino acid residue R140 or a missense mutation at amino acid residue R172. In another aspect, the driver mutation in ASXL1 is a loss-of-function mutation. In another aspect, the loss-of-function mutation in ASXL1 is selected from at least one of a frameshift mutation or a nonsense mutation. In another aspect, the driver mutation in BCOR is a loss-of-function mutation. In another aspect, the loss-of-function mutation in BCOR is selected from at least one of a nonsense mutation or a frameshift mutation. In another aspect, the driver mutation in SETBP1 is a loss-of-function mutation. In another aspect, the loss-of-function mutation in SETBP1 is selected from at least one of a nonsense mutation or a frameshift mutation. In another aspect, the driver mutation in MLL is a gain-of-function mutation. In another aspect, the gain-of-function mutation in MLL is selected from at least one of a PTD or a fusion mutation comprising MLL on chromosome 11 and a fusion partner. In another aspect, the fusion mutation in MLL comprises the fusion of MLL with at least one of EPS15/AF1P, MLLT11/AF1Q, AFF3/LAF4, SEPT2, NCKIPSD/AF3P21, DCP1A, EEFSEC/SELB, GMPS, LPP, FRYL, SEPT11/FLJ10849, AFF1/AF4, SORBS2/ARGBP2, CENPK/FKSG14, AFF4/AF6Q31, ARHGAP26/GRAF, SMAP1, FOXO3/AF6Q21, MLLT4/AF6, TNRC18/KIAA1856, MLLT3/AF9, DAB2IP/AF9Q34, FNBP1/FBP17, LAMC3, ABI1, MLLT10/AF10, NEBL, TET1/LCX, NRIP3, ARHGEF17, C2CD3/DKFZP586P0123, PICALM/CALM, MAML2, UBE4A, ARHGEF12/LARG, CBL, BCL0L, TIRAP, DCPS, CIP29, GPHN, KIAA0284, CASC5/AF16Q14, ZFYVE19/MPFYVE, CREBBP/CBP, GAS7, ACACA, MLLT6/AF17, LASP1, SEPT9/AF17Q25, ELL, SH3GL1/EEN, VAV1, MLLT1/ENL, ASAH3/ACER1, LOC100128568, MYO1F, ACTN4, MAPRE1, SEPTS/CDCREL, EP300/P300, FOXO4/AFX, SETP6, or FLNA. In another aspect, the therapeutically effective amount of Crenolanib or the pharmaceutically acceptable salt thereof are from about 50 to 500 mg per day, 100 to 450 mg per day, 200 to 400 mg per day, 300 to 500 mg per day, 350 to 500 mg per day, or 400 to 500 mg per day; or the therapeutically effective amount of Crenolanib or the pharmaceutically acceptable salt thereof is administered at least one of continuously, intermittently, systemically, or locally; or the therapeutically effective amount of Crenolanib or the pharmaceutically acceptable salt thereof is administered orally, intravenously, or intraperitoneally. In another aspect, the Crenolanib or the pharmaceutically acceptable salt thereof is Crenolanib besylate, Crenolanib phosphate, Crenolanib lactate, Crenolanib hydrochloride, Crenolanib citrate, Crenolanib acetate, Crenolanib toluenesulphonate, and Crenolanib succinate. In another aspect, the method further comprises at least one of: administering up to three times or more a day for as long as the human patient is in need of treatment for the leukemia; or providing at least one of sequentially or concomitantly, with another pharmaceutical agent in a newly diagnosed human leukemia patient, to maintain remission of an existing human leukemia patient, or in a relapsed/refractory human leukemia patient; or providing as a single agent or in combination with another pharmaceutical agent in a patient with a newly diagnosed leukemia, to maintain remission, or in a relapse/refractory human leukemia patient; or providing as a single agent or in combination with another pharmaceutical agent in a newly diagnosed human pediatric leukemia patient, to maintain remission, or in a relapsed/refractory human pediatric leukemia patient. In another aspect, the human patient is relapsed/refractory to another tyrosine kinase inhibitor or chemotherapy.

As embodied and broadly described herein, another aspect of the present disclosure relates to a method for treating a human patient suffering from acute myelogenous leukemia (AML) comprising: obtaining a biological sample from the human patient; determining from the sample that the human patient has AML with a deregulated FLT3 receptor or a constitutively active FLT3 receptor; determining that the AML has one or more driver mutations in one or more epigenetic regulator proteins that results in a loss of normal function of the one or more epigenetic regulator proteins; and then administering to the human patient in need of such treatment for the AML comprising both the deregulated FLT3 receptor or a constitutively active FLT3 receptor and the one or more driver mutations in the one or more epigenetic regulator proteins a therapeutically effective amount of Crenolanib or salt thereof, thereby treating the AML. In one aspect, the FLT3 mutation is selected from at least one of FLT3-ITD or FLT3-TKD. In another aspect, the epigenetic regulator protein is at least one of TET2, IDH1, IDH2, ASXL1, BCOR, SETBP1, or MLL. In another aspect, the driver mutation in TET2 is a loss-of-function mutation. In another aspect, the driver mutation the loss-of-function mutation in TET2 is selected from at least one of a frameshift mutation, a nonsense mutation, or a missense mutation at amino acid residues between D1129 and G1936 inclusive in the catalytic domain. In another aspect, the driver mutation in IDH1 is selected from at least one of a missense mutation at amino acid residue R132. In another aspect, the driver mutation in IDH2 is selected from at least one of a missense mutation at amino acid residue R140 or a missense mutation at amino acid residue R172. In another aspect, the driver mutation in ASXL1 is a loss-of-function mutation. In another aspect, the loss-of-function mutation in ASXL1 is selected from at least one of a frameshift mutation or a nonsense mutation. In another aspect, the driver mutation in BCOR is a loss-of-function mutation. In another aspect, the loss-of-function mutation in BCOR is selected from at least one of a nonsense mutation or a frameshift mutation. In another aspect, the driver mutation in SETBP1 is a loss-of-function mutation. In another aspect, the loss-of-function mutation in SETBP1 is selected from at least one of a nonsense mutation or a frameshift mutation. In another aspect, the driver mutation in MLL is a gain-of-function mutation. In another aspect, the gain-of-function mutation in MLL is selected from at least one of a PTD or a fusion mutation comprising MLL on chromosome 11 and a fusion partner. In another aspect, the fusion mutation in MLL comprises the fusion of MLL with at least one of EPS15/AF1P, MLLT11/AF1Q, AFF3/LAF4, SEPT2, NCKIPSD/AF3P21, DCP1A, EEFSEC/SELB, GMPS, LPP, FRYL, SEPT11/FLJ10849, AFF1/AF4, SORBS2/ARGBP2, CENPK/FKSG14, AFF4/AF6Q31, ARHGAP26/GRAF, SMAP1, FOXO3/AF6Q21, MLLT4/AF6, TNRC18/KIAA1856, MLLT3/AF9, DAB2IP/AF9Q34, FNBP1/FBP17, LAMC3, ABI1, MLLT10/AF10, NEBL, TET1/LCX, NRIP3, ARHGEF17, C2CD3/DKFZP586P0123, PICALM/CALM, MAML2, UBE4A, ARHGEF12/LARG, CBL, BCL0L, TIRAP, DCPS, CIP29, GPHN, KIAA0284, CASC5/AF16Q14, ZFYVE19/MPFYVE, CREBBP/CBP, GAS7, ACACA, MLLT6/AF17, LASP1, SEPT9/AF17Q25, ELL, SH3GL1/EEN, VAV1, MLLT1/ENL, ASAH3/ACER1, LOC100128568, MYO1F, ACTN4, MAPRE1, SEPTS/CDCREL, EP300/P300, FOXO4/AFX, SETP6, or FLNA. In another aspect, the therapeutically effective amount of Crenolanib or the pharmaceutically acceptable salt thereof are from about 50 to 500 mg per day, 100 to 450 mg per day, 200 to 400 mg per day, 300 to 500 mg per day, 350 to 500 mg per day, or 400 to 500 mg per day; or the therapeutically effective amount of Crenolanib or the pharmaceutically acceptable salt thereof is administered at least one of continuously, intermittently, systemically, or locally; or the therapeutically effective amount of Crenolanib or the pharmaceutically acceptable salt thereof is administered orally, intravenously, or intraperitoneally. In another aspect, the Crenolanib or the pharmaceutically acceptable salt thereof is Crenolanib besylate, Crenolanib phosphate, Crenolanib lactate, Crenolanib hydrochloride, Crenolanib citrate, Crenolanib acetate, Crenolanib toluenesulphonate, and Crenolanib succinate. In another aspect, the method further comprises at least one of: administering up to three times or more a day for as long as the human patient is in need of treatment for the leukemia; or providing at least one of sequentially or concomitantly, with another pharmaceutical agent in a newly diagnosed human leukemia patient, to maintain remission of an existing human leukemia patient, or in a relapsed/refractory human leukemia patient; or providing as a single agent or in combination with another pharmaceutical agent in a patient with a newly diagnosed leukemia, to maintain remission, or in a relapse/refractory human leukemia patient; or providing as a single agent or in combination with another pharmaceutical agent in a newly diagnosed human pediatric leukemia patient, to maintain remission, or in a relapsed/refractory human pediatric leukemia patient. In another aspect, the human patient is relapsed/refractory to another tyrosine kinase inhibitor or chemotherapy.

As embodied and broadly described herein, another aspect of the present disclosure relates to a method for specifically inhibiting a deregulated or constitutively active FLT3 receptor tyrosine kinase, comprising: obtaining a sample from a human patient having acute myelogenous leukemia (AML); determining that the AML has a FLT3 receptor tyrosine kinase that is deregulated or constitutively active and one or more driver mutations in one or more epigenetic regulator proteins that results in a loss of normal function of the one or more epigenetic regulator proteins by performing or having performed genetic testing on the sample from the patient, wherein these mutations cause a poor prognosis; and administering a therapeutically effective amount of Crenolanib or a salt thereof, sufficient to eliminate the AML, to the human patient in need of such treatment for AML with both the deregulated or constitutively active FLT3 receptor tyrosine kinase and the one or more driver mutations in the one or more epigenetic regulator proteins. In one aspect, the FLT3 mutation is selected from at least one of FLT3-ITD or FLT3-TKD. In another aspect, the epigenetic regulator protein is at least one of TET2, IDH1, IDH2, ASXL1, BCOR, SETBP1, or MLL. In another aspect, the driver mutation in TET2 is a loss-of-function mutation. In another aspect, the driver mutation the loss-of-function mutation in TET2 is selected from at least one of a frameshift mutation, a nonsense mutation, or a missense mutation at amino acid residues between D1129 and G1936 inclusive in the catalytic domain. In another aspect, the driver mutation in IDH1 is selected from at least one of a missense mutation at amino acid residue R132. In another aspect, the driver mutation in IDH2 is selected from at least one of a missense mutation at amino acid residue R140 or a missense mutation at amino acid residue R172. In another aspect, the driver mutation in ASXL1 is a loss-of-function mutation. In another aspect, the loss-of-function mutation in ASXL1 is selected from at least one of a frameshift mutation or a nonsense mutation. In another aspect, the driver mutation in BCOR is a loss-of-function mutation. In another aspect, the loss-of-function mutation in BCOR is selected from at least one of a nonsense mutation or a frameshift mutation. In another aspect, the driver mutation in SETBP1 is a loss-of-function mutation. In another aspect, the loss-of-function mutation in SETBP1 is selected from at least one of a nonsense mutation or a frameshift mutation. In another aspect, the driver mutation in MLL is a gain-of-function mutation. In another aspect, the gain-of-function mutation in MLL is selected from at least one of a PTD or a fusion mutation comprising MLL on chromosome 11 and a fusion partner. In another aspect, the fusion mutation in MLL comprises the fusion of MLL with at least one of EPS15/AF1P, MLLT11/AF1Q, AFF3/LAF4, SEPT2, NCKIPSD/AF3P21, DCP1A, EEFSEC/SELB, GMPS, LPP, FRYL, SEPT11/FLJ10849, AFF1/AF4, SORBS2/ARGBP2, CENPK/FKSG14, AFF4/AF6Q31, ARHGAP26/GRAF, SMAP1, FOXO3/AF6Q21, MLLT4/AF6, TNRC18/KIAA1856, MLLT3/AF9, DAB2IP/AF9Q34, FNBP1/FBP17, LAMC3, ABI1, MLLT10/AF10, NEBL, TET1/LCX, NRIP3, ARHGEF17, C2CD3/DKFZP586P0123, PICALM/CALM, MAML2, UBE4A, ARHGEF12/LARG, CBL, BCL0L, TIRAP, DCPS, CIP29, GPHN, KIAA0284, CASC5/AF16Q14, ZFYVE19/MPFYVE, CREBBP/CBP, GAS7, ACACA, MLLT6/AF17, LASP1, SEPT9/AF17Q25, ELL, SH3GL1/EEN, VAV1, MLLT1/ENL, ASAH3/ACER1, LOC100128568, MYO1F, ACTN4, MAPRE1, SEPTS/CDCREL, EP300/P300, FOXO4/AFX, SETP6, or FLNA. In another aspect, the therapeutically effective amount of Crenolanib or the pharmaceutically acceptable salt thereof are from about 50 to 500 mg per day, 100 to 450 mg per day, 200 to 400 mg per day, 300 to 500 mg per day, 350 to 500 mg per day, or 400 to 500 mg per day; or the therapeutically effective amount of Crenolanib or the pharmaceutically acceptable salt thereof is administered at least one of continuously, intermittently, systemically, or locally; or the therapeutically effective amount of Crenolanib or the pharmaceutically acceptable salt thereof is administered orally, intravenously, or intraperitoneally. In another aspect, the Crenolanib or the pharmaceutically acceptable salt thereof is Crenolanib besylate, Crenolanib phosphate, Crenolanib lactate, Crenolanib hydrochloride, Crenolanib citrate, Crenolanib acetate, Crenolanib toluenesulphonate, and Crenolanib succinate. In another aspect, the method further comprises at least one of: administering up to three times or more a day for as long as the human patient is in need of treatment for the leukemia; or providing at least one of sequentially or concomitantly, with another pharmaceutical agent in a newly diagnosed human leukemia patient, to maintain remission of an existing human leukemia patient, or in a relapsed/refractory human leukemia patient; or providing as a single agent or in combination with another pharmaceutical agent in a patient with a newly diagnosed leukemia, to maintain remission, or in a relapse/refractory human leukemia patient; or providing as a single agent or in combination with another pharmaceutical agent in a newly diagnosed human pediatric leukemia patient, to maintain remission, or in a relapsed/refractory human pediatric leukemia patient. In another aspect, the human patient is relapsed/refractory to another tyrosine kinase inhibitor or chemotherapy.

This summary of the invention does not necessarily describe all necessary features of the invention.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention comprises the use of the compounds of the present invention to treat disorders related to FLT3 kinase activity or expression in a subject.

Crenolanib (4-Piperidinamine, 1-[2-[5-[(3-methyl-3-oxetanyl) methoxy]-1H-benzimidazol-1-yl]-8-quinolinyl]) and its pharmaceutically acceptable salts, are protein tyrosine kinase inhibitors selective for constitutively active FLT3 mutations, including FLT3 ITD and FLT3 TKD mutations. Unlike prior FLT3 inhibitors in the art, the besylate salt form of Crenolanib has been shown to be remarkably effective in depleting circulating peripheral blood blast percentages and bone marrow blast percentages in heavily pretreated FLT3 mutant AML patients without significantly increasing patient QT prolongation. Crenolanib is currently being investigated for use in the treatment of patients with relapsed or refractory constitutively activated FLT3 mutated primary AML or AML secondary to myelodysplastic syndrome.

An analysis of Crenolanib's efficacy in patients presenting with concomitant FLT3 mutations, as well as other cytogenetic or molecular abnormalities, are also presently being developed through ongoing clinical trials.

Crenolanib safety and tolerability was evaluated between November 2003 and September 2006 in a phase I first-in-human dose-escalation single agent study in heavily pretreated patients with advanced solid tumors (Protocol A5301001(Lewis et al., 2009). Fifty-nine patients were enrolled and completed the study. Most treatment related adverse events were of grade 1 or 2 severity. There was no evidence of cumulative toxicity. In patients treated with lower drug dosages ranging from 60-200 mg once daily, the most common adverse events observed were grade 1 nausea and vomiting, which usually occurred approximately 45 minutes after dosing. There were no grade 3 or 4 toxicities in these patients. At higher doses 280 mg and 340 mg once daily, liver enzyme elevations were the most severe side effects. Liver enzyme levels returned to normal following the discontinuation of Crenolanib. The present invention has demonstrated that the administration of 100 mg three times daily of Crenolanib besylate to human patients diagnosed with constitutively activated FLT3 mutant relapsed or refractory AML does not always result in an elevation of liver enzymes. It also demonstrates that when liver enzymes are elevated that liver enzyme levels can be decreased by discontinuing the drug for approximately 1 week and re-starting Crenolanib at a reducing dosage of 80 mg three times daily.

No grade 2/3/4 QT prolongation was observed in any of the 59 patients treated in the phase I dose escalation safety study, despite Crenolanib dose received. Similarly, there have been no significant differences in baseline QT prolongation and on-treatment QT prolongation in a currently ongoing pediatric glioma trial with twenty-four children being treated with the besylate form of Crenolanib. Likewise, the present invention has shown no cases of QT prolongation following the administration of 100 mg of Crenolanib besylate three times daily to human patients diagnosed with constitutively activated FLT3 mutant relapsed or refractory AML. Other FLT3 inhibitors known in the art have caused significant QTc prolongation leading to strict clinical study inclusion and exclusion criteria to prevent severe adverse events. For example, two separate quizartinib AML studies have revealed that the compound causes significant Q prolongation. In a 76 patient phase I, single-agent study evaluating the compound in both FLT3 wildtype and FLT ITD mutated relapsed and refractory AML identified QT prolongation as the dose-limiting toxicity. (Jorge Cortes et al., 2009). Additionally, interim data from a phase II trial of quizartinib monotherapy in 62 patients with relapsed or refractory AML with FLT3 ITD activating mutations asymptomatic QT prolongation was one of the most common (>19%) drug-related adverse events. QT prolongation of all grades occurred in 21 (34%) patients. More than half of the QT prolongation events recorded were grade 3 (18%). Reducing the starting dose of quizartinib by greater than 30% did not alleviate all cases of QT prolongation. (J. Cortes et al., 2011).

The present invention includes methods of treating proliferative disorders in a subject. In one embodiment, the present invention includes a method for treating a human patient having leukemia with Crenolanib, wherein the human patient is suffering from FLT3 mutated leukemia, the method comprising: determining whether the human patient has a poor prognosis for the FLT3 mutated leukemia by: obtaining or having obtained a leukemia sample from the human patient; and performing or having performed a genotyping assay on the biological sample to determine if the human patient has both a mutated FLT3 or a constitutively active FLT3 mutant and one or more mutations in an epigenetic regulator gene, wherein the presence of both the mutated FLT3 and the one or more mutations in an epigenetic regulator gene indicates that the patient has a poor prognosis; and if the human patient has the poor prognosis administering to the patient a therapeutically effective amount of Crenolanib or a pharmaceutically acceptable salt thereof, to treat the leukemia. In another embodiment, the present invention includes a method for treating a human patient suffering from a leukemia comprising: identifying that the human patient is in need of therapy for the leukemia, wherein the leukemia comprises both a deregulated FLT3 receptor tyrosine kinase and a mutation in an epigenetic regulator gene, and wherein the leukemia is characterized by having a poor prognosis; and administering to the patient a therapeutically effective amount of Crenolanib or a salt thereof sufficient to treat the leukemia. In another embodiment, the present invention includes a method for treating a human patient suffering from acute myelogenous leukemia (AML) comprising: obtaining a sample from the human patient; determining from the sample that the human patient has AML with a deregulated FLT3 receptor or a constitutively active FLT3 receptor; determining if the AML has one or more mutations in an epigenetic regulator gene; and if the AML has both the deregulated FLT3 receptor or a constitutively active FLT3 receptor and the mutation in an epigenetic regulator gene, then administering to the human patient in need of such treatment a therapeutically effective amount of Crenolanib or salt thereof. In another embodiment, the present invention includes a method for specifically inhibiting a deregulated or constitutively active FLT3 receptor tyrosine kinase, comprising: obtaining a sample from a human patient having acute myelogenous leukemia (AML); determining that the AML has a FLT3 receptor tyrosine kinase that is deregulate or constitutively active and one or more mutations in an epigenetic regulator gene; wherein the AML with both the deregulated or constitutively active FLT3 receptor tyrosine kinase and the one or more mutations in an epigenetic regulator gene cause a poor prognosis; and if the human patient has AML with both the deregulate or constitutively active FLT3 receptor tyrosine kinase and the one or more mutations in an epigenetic regulator gene, administering to the human patient in need of such treatment a therapeutically effective amount of Crenolanib or a salt thereof, sufficient to eliminate the AML.

The present invention includes methods of treating proliferative disorders in a subject. In one embodiment, the present invention includes a method for treating a human patient having leukemia with Crenolanib, wherein the human patient is suffering from FLT3 mutated leukemia, the method comprising: determining whether the human patient has a poor prognosis for the FLT3 mutated leukemia by: obtaining or having obtained a leukemia sample from the human patient; and performing or having performed a genotyping assay on the biological sample to determine if the human patient has both a mutated FLT3 or a constitutively active FLT3 mutant and one or more mutations in an epigenetic regulator gene, wherein the presence of both the mutated FLT3 and the one or more mutations in an epigenetic regulator indicates that the patient has a poor prognosis; and if the human patient has the poor prognosis administering to the patient a therapeutically effective amount of Crenolanib or a pharmaceutically acceptable salt thereof, to treat the leukemia. In another embodiment, the present invention includes a method for treating a human patient suffering from a leukemia comprising: identifying that the human patient is in need of therapy for the leukemia, wherein the leukemia comprises both a deregulated FLT3 receptor tyrosine kinase and a mutation in an epigenetic regulator gene selected from TET2, IDH1, IDH2, ASXL1, BCOR, SETBP1, or MLL, and wherein the leukemia is characterized by having a poor prognosis; and administering to the patient a therapeutically effective amount of Crenolanib or a salt thereof sufficient to treat the leukemia. In another embodiment, the present invention includes a method for treating a human patient suffering from acute myelogenous leukemia (AML) comprising: obtaining a sample from the human patient; determining from the sample that the human patient has AML with a deregulated FLT3 receptor or a constitutively active FLT3 receptor; determining if the AML has one or more mutations in an epigenetic regulator gene selected from TET2, IDH1, IDH2, ASXL1, BCOR, SETBP1, or MLL; and if the AML has both the deregulated FLT3 receptor or a constitutively active FLT3 receptor and the mutation in an epigenetic regulator gene, then administering to the human patient in need of such treatment a therapeutically effective amount of Crenolanib or salt thereof. In another embodiment, the present invention includes a method for specifically inhibiting a deregulated or constitutively active FLT3 receptor tyrosine kinase, comprising: obtaining a sample from a human patient having acute myelogenous leukemia (AML); determining that the AML has a FLT3 receptor tyrosine kinase that is deregulate or constitutively active and one or more mutations in an epigenetic regulator gene selected from TET2, IDH1, IDH2, ASXL1, BCOR, SETBP1, or MLL; wherein the AML with both the deregulated or constitutively active FLT3 receptor tyrosine kinase and the one or more mutations in an epigenetic regulator gene cause a poor prognosis; and if the human patient has AML with both the deregulate or constitutively active FLT3 receptor tyrosine kinase and the one or more mutations in an epigenetic regulator gene, administering to the human patient in need of such treatment a therapeutically effective amount of Crenolanib or a salt thereof, sufficient to eliminate the AML.

The present inventor recognized that multiple studies have demonstrated that patients with both FLT3 and epigenetic regulator mutations have worse outcomes than patients with either mutation alone. Epigenetic regulators include proteins with functions related to control of gene expression, including chromatin remodeling, DNA methylation, and histone methylation or acetylation. (Al Aboud, Tupper, & halal, 2021). These changes activate or repress the expression of target genes by changing the accessibility of the promoter region to transcription factors. In contrast to FLT3, in which activating mutations are oncogenic, mutations in epigenetic regulators result in loss-of-function, or in some cases neomorphic mutations in which there is a loss of normal gene function and gain of a new gene function, are oncogenic. (Sun, Chen, & Deshpande, 2018). Epigenetic regulators with recurrent mutations in hematologic malignancies include TET2 (Ten Eleven Methylcytosine Dioxygenase 2), IDH1 (Isocitrate Dehydrogenase 1), IDH2 (Isocitrate Dehydrogenase 2), ASXL1 (Additional Sex Comb-Like 1), BCOR (BCL-6 Co-Repressor), SETBP1 (SET-Binding Protein 1), and MLL/KMT2A (Mixed Lineage Leukemia, also called Histone-lysine N-Methyltransferase 2A).

TET2, or Ten Eleven Methylcytosine Dioxygenase 2, is a 2-oxoglutarate and Fe(II) dependent dioxygenase that converts 5-methylcytosein to 5-hydroxymethylcytosine, which induces replacement of the methylated cytosine with unmodified cytosine by DNA repair machinery, making TET2 a key component of DNA demethylation. (Aslanyan et al., 2014). The TET2 protein catalytic domain is formed from 4 main sub-domains: the double-stranded 13 helix domain; the cysteine-rich domain; and binding sites for 2-oxoglutarate and Fe(II), which flank the double-stranded 13 helix domain. (Rasmussen & Helin, 2016). The catalytic domain is composed of amino acids between D1129 and G1936, inclusive. (Ferrone, Blydt-Hansen, & Rauh, 2020). Mutations in TET2 are found in approximately 20-25% of MDS patients, 10-15% of MPN patients, up to 50% of CMML patients, and 8-32% of AML patients. (Rasmussen & Helin, 2016).

Frameshift mutations represent the most common TET2 mutations found in AML. These mutations insert or delete a number of base pairs that is not a multiple of three, thereby disrupting the normal reading frame of TET and resulting in a nonfunctional protein. However, other mutations within TET2, such as nonsense (and early stop codon resulting in a non-functional truncated protein), or missense mutations in the catalytic domain have also been identified. (Ferrone et al., 2020; Papaemmanuil et al., 2016). These missense mutations in the catalytic domain also results in a loss-of-function of TET2 by disrupting DNA binding. (Ferrone et al., 2020). Therefore, all three types of mutations identified in TET2, frameshift, nonsense, and missense mutations in the catalytic domain, result in loss-of-function of TET2. Table 1 below contains an analysis of the TET2 mutations found by Papaemmanuil et al.

TABLE 1

TET2 Mutations by Type Identified by Papaemmanuil

| Mutation Type | n | Percentage of TET2 Mutations |
|---|---|---|
| Frameshift | 75 | 36.6% |
| Nonsense | 61 | 29.8% |
| Missense in Catalytic Domain | 45 | 22.0% |

The functional consequences of TET2 loss have been extensively studied in animal models. Loss of TET2 results induces myeloproliferative neoplasms in transgenic mice by disrupting hematopoietic homeostasis. (Quivoron et al., 2011). In models of loss-of-function TET2 mutations carried in tandem with activating FLT3 mutations, resulted in AML-like disease in transgenic animals, with full penetrance. (Rasmussen & Helin, 2016). These results in animal models show that loss-of-function TET2 mutations and activating FLT3 mutations cooperate during leukemogenesis. Furthermore, studies in human patients with both TET2 and FLT3 mutations have found these patients to have a worse prognosis and shorter survival than patients without these co-occurring mutations. (Aslanyan et al., 2014).

IDH1, or isocitrate dehydrogenase 1, catalyzes the oxidative decarboxylation of isocitrate to α-ketoglutarate. Proteins involved in histone modification and other epigenetic functions, such as TET2 are dependent on α-ketoglutarate, and loss or change in function of IDH can impact normal epigenetic regulation. (Chen et al., 2019; Dang et al., 2009; Sun et al., 2018). IDH1 is comprised of two large and two small domains, which flank the central claps domain. (Venney, Mohd-Sarip, & Mills, 2021). Mutations in IDH1 occur in 15-27% of AML cases. (Boddu et al., 2017).

All identified IDH1 mutation in myeloid malignancies and other proliferative disorders are missense mutations at amino acid residue R132 in the small domain. (Papaemmanuil et al., 2016; Tyner et al., 2018). Mutations at this residue abolish magnesium binding, which is necessary for the conversion of isocitrate to α-ketoglutarate. (Dang et al., 2009). IDH1-R132 mutations are neomorphic, that is there is a loss of normal gene function but an atypical new function is present. In the case of IDH1, that neomorphic function is the conversion of isocitrate to 2-hydroxyglutarate. The mutant IDH1 causes a build-up of 2-hydroxyglutarate in the cells, which causes epigenetic dysregulation and similar effects to TET2 loss, including hypermethylation and differentiation block. (Chen et al., 2019; Dang et al., 2009).

In mouse models using conditional knock-in of the IDH-R132 mutation in hematopoietic cells, mice developed signs of a dysfunctional bone marrow and pre-leukemic signatures including differentiation blocks, splenomegaly, and extramedullary hematopoiesis. (Sasaki et al., 2012). While these transgenic mice did not develop AML with full penetrance, they did develop MDS-like conditions, which is consistent with the two-hit model of tumorigenesis. In other words, while IDH1 mutations alone do not seem to be sufficient for leukemogenesis, additional mutations in other genes such as FLT3 may provide the necessary dysregulation for full AML development. In cell lines, FLT3, activates mutant IDH1 through phosphorylation of tyrosine residues on IDH1. (Chen et al., 2021). High FLT3 signaling though activating FLT3 mutations would increase this effect. Moreover, in human AML patients, the co-occurrence of IDH1-R132 and activating FLT3 mutations is associated with a worse prognosis than either mutation alone. (Boddu et al., 2017).

IDH2, or isocitrate dehydrogenase 2, catalyzes the oxidative decarboxylation of isocitrate to α-ketoglutarate, much like IDH1. However, IDH2 is confined to the mitochondria while IDH1 is expressed in the cytosol. Therefore, in addition to the large, small, and clasp domains that are present in IDH1, IDH2 also contains a mitochondrial target sequence. (Venney et al., 2021). Mutations in IDH2 are found in 9-13% of AML patients, with mutations also seen in glioma, cholangiocarcinoma, and various sarcomas. (Choe et al., 2020).

Missense mutations at amino acid residues R140 or R172 are the most common IDH2 mutations found in proliferative disorders. In AML, missense mutations at R140 represent 72.4% of all IDH3 mutations with R172 mutations accounting for 26.3%. (Papaemmanuil et al., 2016). Similarly to IDH1, these mutations are neomorphic, with mutant IDH2 losing the normal function of converting isocitrate to α-ketoglutarate, and instead resulting in a buildup of 2-hydroxyglutarate, which disrupts α-ketoglutarate dependent epigenetic regulation by TET2 and other proteins. (Chen et al., 2021).

The IDH2-R140 mutation is directly analogous to the R132 mutation in IDH1. The R172 mutation disrupts substrate binding and results in loss-of-function. In the case of IDH2, FLT3 signaling optimizes mutant IDH2-R140 function, by providing a slight inhibitive regulation that prevents the accumulation of 2-hyroxyglutarate to toxic levels and instead maintaining the level that is tumorigenic. (Chen et al., 2021). The functional consequence of either type of IDH2 mutation, R140 or R172, is lower levels of α-ketoglutarate, which results in decreased TET2 signaling and a similar phenotype (hypermethylation and differentiation block) as loss-of-function TET2 mutations. Moreover, the co-occurrence of IDH2 mutations and activating FLT3 mutations in patients results in a worse prognosis than either mutation alone, and FLT3 mutations are a mechanism of resistance to IDH2 inhibitors. (Choe et al., 2020).

ASXL1, or Additional Sex Comb-Like 1, is a chromatin remodeling protein that acts as a coactivator for retinoic acid receptor. ASXL1 is also involved in histone acetylation mediated gene regulation. (Cho, Kim, Park, Sin, & Um, 2006; Gelsi-Boyer et al., 2012). ASX1 contains a conserved PHD finger domain (plant homeodomain), a helix-turn-helix domain, and a deubiquitinase adapter domain. The PHD finger domain is responsible for binding to histones, and ASXL1 acts as part of a complex of other regulatory proteins to control gene expression, including silencing of HOX genes, which are aberrantly expressed in many cancers. (Venney et al., 2021) Mutations in ASXL1 are found in 11-23% of AML and are also present in other hematological malignancies. (Pratcorona et al., 2012).

Frameshift and nonsense mutations represent the most common ASXL1 mutations found in proliferative disorders. These mutations result in nonfunctional proteins by either shifting the reading frame or inserting an early stop codon that creates a truncated protein. These mutations result in loss of part of all of the PHD domain, preventing ASXL1 binding to histones. (Papaemmanuil et al., 2016; Pratcorona et al., 2012; Venney et al., 2021). Overall, frameshift mutations represent 50% of all ASXL1 mutations found in AML, with nonsense mutations accounting for an additional 37%.

The functional consequences of ASXL1 loss have been studied in preclinical models of both cell lines and animal models. Loss of ASXL1 results in abnormally high expression of HOX gene clusters. Overexpression of these genes confers a poorer prognosis and has a deleterious effect on normal differentiation. (Venney et al., 2021). While loss of ASXL1 alone is not always sufficient to for leukemogenesis, when present in combination with activating mutations in signaling pathways, such as NRAS or FLT3, transgenic mice develop hematological malignancies with high penetrance. (Abdel-Wahab et al., 2012). Finally, human AML patients with ASX1 mutations carry a particularly poor prognosis, with less than half of patients expected to survive longer than 16 months from initial diagnosis. (Pratcorona et al., 2012).

BCOR, or B-cell Corepressor, is a transcriptional corepressor which inhibits gene expression when recruited to promoter regions by DNA-binding proteins such as BCL6 or MLLT3. BCOR associates with histone deacetylases to regulate gene expression. (Kelly et al., 2019). BCOR contains a BCL6 binding domain, a MLLT3 binding domain, ANK repeats, and a PCGF1 binding region. (Astolfi et al., 2019). Mutations in BCOR are found in approximately 5% of AML patients. (Eckardt et al., 2021).

Frameshift or nonsense mutations represent all mutations found in BCOR. Both of these types of mutations cause a loss-of-function by either shifting the reading frame or inserting an early stop codon that results in a truncated protein. In human AML patients, 55.6% of BCOR mutations are frameshift, with the remaining 44.4% of mutations being nonsense mutations. (Papaemmanuil et al., 2016). As BCOR is a corepressor of gene expression, loss-of-function mutations in BCOR result in aberrant expression of genes involved in cell growth and proliferation, which contributes to leukemogenesis.

The functional consequences of loss of BCOR have been investigated in transgenic animal models. While the loss of BCOR alone is not always sufficient for leukemogenesis, loss of BCOR in combination with activating mutations in signaling pathways, such as KRAS or FLT3, result in an aggressive and transplantable acute leukemia. (Kelly et al., 2019). Furthermore, in humans, the presence of a BCOR mutation is associated with shortened survival, with at least half of patients expected to die within two years of initial diagnosis. (Zhang et al., 2020).

SETBP1, or SET-binding protein 1, is a DNA binding protein that functions as part of a complex of proteins to demethylate chromatin, leading to gene upregulation. (Piazza et al., 2018). SETBP1 contains three AT hook domains, a SKI homologous region, a SET-binding domain, and a repeat domain at the C-terminus. The SKI homologous region is between amino acid residues E706 and H917, inclusive, and is the most common hotspot region for mutations to occur. (Thol et al., 2013). SETBP1 mutations are found in 3-5% of patients with MDS or AML, and are also found in other hematological malignancies such as CML. (Hou et al., 2014; Piazza et al., 2018).

Mutations in SETBP1 are typically missense mutations, in which one amino acid is replaced with another, within the SKI homologous region. Hotspot residues include G870, D868, 1871, E858, and 5867. (Hou et al., 2014). Missense mutations in this region disrupt ubiquitination and degradation, resulting in hypomethylation of target genes and dysregulated expression of said target genes, including genes involved in cell differentiation and tissue development. (Piazza et al., 2018).

The functional consequence of SETBP1 missense mutations in the SKI homologous region has been investigated in animal models. Recurrent mutation at 1871 or D868 are sufficient to induce AML in mouse xenografts, and result in increased expression of the known oncogene MYB. (Nguyen et al., 2016). Furthermore, in older human patients with AML, SETBP1 mutations carry an especially poor prognosis, with half of patients expected to die within 3 months of diagnosis. (Cristobal et al., 2010).

MLL (Mixed Lineage Leukemia), also known as KMT2A (Histone-lysin N-methyltransferase 2A), is a histone methyltransferase that catalyzes the methylation of lysines in histones H3 and H4. MLL contains a SET domain, which binds to histone H3, a transactivation domain, PHD domains, a DNA methyltransferase (catalytic) domain, and AT hooks. During normal functions, MLL forms a complex with a number of other nuclear proteins, including CREBBP, MOF, ASH2L, RbBP5, and WDR5, to activate transcription of target genes. Mutations in MLL are found in 6-18% of AML patients. (Bill et al., 2020; Yu, Li, Zhang, Wan, & Jiang, 2020).

Unlike the recurrent mutations in other epigenetic regulators disclosed herein, the mutations in MLL are typically either partial tandem duplications (PTD) or fusion mutations with another gene, the result of translocations or inversions involving chromosome 11. MLL-PTD mutations are found in approximately 3-11% of AML cases and are more common than fusion proteins, which are found in 3-7% of AML patients. (Bill et al., 2020; Yu et al., 2020). Identified fusion partners of MLL include EPS15/AF1P, MLLT11/AF1Q, AFF3/LAF4, SEPT2, NCKIPSD/AF3P21, DCP1A, EEFSEC/SELB, GMPS, LPP, FRYL, SEPT11/FLJ10849, AFF1/AF4, SORBS2/ARGBP2, CENPK/FKSG14, AFF4/AF6Q31, ARHGAP26/GRAF, SMAP1, FOXO3/AF6Q21, MLLT4/AF6, TNRC18/KIAA1856, MLLT3/AF9, DAB2IP/AF9Q34, FNBP1/FBP17, LAMC3, ABI1, MLLT10/AF10, NEBL, TET1/LCX, NRIP3, ARHGEF17, C2CD3/DKFZP586P0123, PICALM/CALM, MAML2, UBE4A, ARHGEF12/LARG, CBL, BCL0L, TIRAP, DCPS, CIP29, GPHN, KIAA0284, CASC5/AF16Q14, ZFYVE19/MPFYVE, CREBBP/CBP, GAS7, ACACA, MLLT6/AF17, LASP1, SEPT9/AF17Q25, ELL, SH3GL1/EEN, VAV1, MLLT1/ENL, ASAH3/ACER1, LOC100128568, MYO1F, ACTN4, MAPRE1, SEPTS/CDCREL, EP300/P300, FOXO4/AFX, SETP6, or FLNA (for genes that have been identified with two separate names, these are indicated by a forward slash). (Meyer et al., 2013; Meyer et al., 2009). The normal cellular function of the identified MLL fusion partners vary, with some being nuclear and some cytoplasmic. However, once fused with MLL, fusion products form complexes in the nucleus, irrespective of the normal localization of the fusion partner. (Winters & Bernt, 2017). This complex formation is important in MLL activation, and also stabilizes the fusion. The functional consequence of MLL fusions proteins is therefore fusion partner agnostic.

For both types of abnormalities, PTD and fusions, the functional consequence is a gain-of-function. MLL is a positive epigenetic regulator of HOX cluster genes, and gain-of-function mutations in MLL result in overexpression of these genes, which are oncogenic and lead to abnormal hematopoiesis and self-renewal. (Winters & Bernt, 2017). This is the same functional cellular consequence as loss-of-function mutations in ASXL1. Since ASXL1 negatively controls HOX expression, loss-of-function mutations result in overexpression of HOX, while MLL positively controls HOX expression, and therefore gain-of-function mutations result in overexpression of HOX. The outcomes on the cellular level are the same.

The effects of MLL mutations in animal models have been investigated. In transgenic mice, the co-occurrence of MLL-PTD mutations and FLT3-ITD mutations results in an aggressive AML with 100% penetrance. (Zorko et al., 2012) Moreover, in human patients the presence of both MLL-PTD mutations and FLT3-ITD mutations are an especially poor prognosis marker, with half of the patients expected to die within 1 year of diagnosis. (Papaemmanuil et al., 2016).

In addition to the poor prognostic effects of mutations in each of the epigenetic regulator genes mentioned herein, the number of mutations, regardless of which specific genes are involved, is associated with poor prognosis. Patients with 3-4 driver mutations have worse outcomes than patients with 1-2, and patients with 7 or more driver mutations have extremely poor outcomes, with less than 20% of patients surviving at 2 years after diagnosis. (Papaemmanuil et al., 2016).

As used herein, the term "poor prognosis" refers to a decreased chance of survival (for example, decreased overall survival, relapse-free survival, or metastasis-free survival). For example, a poor prognosis has a decreased chance of survival includes a survival time of equal to or less than 60 months, such as 50 months, 40 months, 30 months, 20 months, 12 months, 6 months, or 3 months from time of diagnosis or first treatment or remission.

By contrast, a "good prognosis" refers to an increased chance of survival, for example increased overall survival, relapse-free survival, or metastasis-free survival. For example, a good prognosis has an increased chance of survival includes a survival time of at least 60 months from time of diagnosis, such as 60 months, 80 months, 100 months, 120 months, 150 months, or more from time of diagnosis or first treatment.

Detection of the mutated FLT3 and/or one or more genetic abnormalities can be performed using any suitable means known in the art. For example, detection of gene mutations can be accomplished by detecting nucleic acid molecules (such as DNA) using nucleic acid amplification methods (such as RT-PCR) or high-throughput sequencing (i.e., "next-generation sequencing"). Detection of chromosomal abnormalities can also be accomplished using karyotyping or in situ hybridization that detect structural and numerical alterations.

In mutated FLT3 tumors, the alteration in expression or presence of one or more genetic abnormalities, such as, e.g., chromosomal translocations, deletions, alternative gene splicing, mutations, or deletions within coding or intron-exon boundary regions, can lead to a measurable decrease in prognosis. In addition to a pre-existing FLT3 mutation, the additional genetic abnormalities disclosed herein significantly decrease the prognosis of the patient. A poor prognosis can refer to any negative clinical outcome, such as, but not limited to, a decrease in the likelihood of survival (such as overall survival, relapse-free survival, or metastasis-free survival), a decrease in the time of survival (e.g., less than 5 years, or less than one year), presence of a malignant tumor, an increase in the severity of disease, a decrease in response to therapy, an increase in tumor recurrence, an increase in metastasis, or the like. In particular examples, a poor prognosis is a decreased chance of survival (for example, a survival time of equal to or less than 60 months, such as 50 months, 40 months, 30 months, 20 months, 12 months, 6 months, or 3 months from time of diagnosis or first treatment).

In other embodiments of the method, the presence of the one or more loss-of-function mutations in TET2, ASXL1, BCOR, neomorphic mutations in IDH1 or IDH2, mutations in the SKI homologous region of SETBP1, or PTD or fusion mutations in MLL (in addition to the FLT3 mutation) in the tumor sample relative to a control indicates a poor prognosis for the patient with the tumor. The method includes detecting the presence of one or more loss-of-function mutations in TET2, ASXL1, BCOR, neomorphic mutations in IDH1 or IDH2, mutations in the SKI homologous region of SETBP1, or PTD or fusion mutations in MLL, using genetic sequencing techniques known in the art to determine if a sample has one of the specified mutations in epigenetic regulators.

As used herein, the phrases "mutations responsible for cancer" and "driver mutations" are used interchangeably to refer to mutations that are present in cancer tissues and which are capable of inducing carcinogenesis of cells. Generally, if a mutation is found in a cancer tissue in which no other known oncogene mutations exists (in other words, if a mutation exists in a mutually exclusive manner with known oncogene mutations), then the mutation can be determined to be a responsible mutation for cancer, and thus, a "driver mutation". Driver mutations within TET include frameshift mutations, nonsense mutations, or missense mutations within the catalytic domain. Driver mutations within IDH1 include missense mutations at amino acid residue R132. Driver mutations in IDH2 include missense mutations at amino acid residues R140 or R172. Driver mutations in ASXL1 include frameshift or nonsense mutations. Driver mutations in BCOR include frameshift or nonsense mutations. Driver mutations in SETBP1 include missense mutations in the SKI homologous region between amino acid residues E706 and H917, inclusive. Driver mutations in MLL include PTD mutations and gene fusions.

In one embodiment, the present invention provides a method for reducing or inhibiting the kinase activity of FLT3 in a subject comprising the step of administering a compound of the present invention to the subject.

As used herein, the term "subject" or "patient" are used interchangeable to refer to an animal, such as a mammal or a human, who has been the object of medical treatment, observation or experiment. In one embodiment to this aspect, the present invention provides a method for reducing or inhibiting the kinase activity of FLT3 in a subject comprising the step of administering a compound of the present invention to the subject. A "subject" refers to an animal, such as a mammal or a human, who has been the object of treatment, observation or experiment.

In other embodiments to this aspect, the present invention provides therapeutic methods for treating a subject with a cell proliferative disorder driven by aberrant kinase activity of mutant FLT3. In one example, the invention provides methods for treating a cell proliferative disorder related to mutant FLT3, comprising administration of a therapeutically effective amount of a pharmaceutical composition comprising a compound of the present invention in a subject. Administration of said therapeutic agent can occur upon manifestation of symptoms characteristic of the FLT3 driven cell proliferative disorder, such that a disease or disorder treated.

As used herein, the term "therapeutically effective amount" refers to an amount of active compound or pharmaceutical salt that elicits the biological or medicinal response in a subject that is being sought by a researcher, veterinarian, medical doctor or other clinician, which includes alleviation of the symptoms of the disease or disorder being treated.

Methods for determining therapeutically effective doses for pharmaceutical compositions comprising a compound of the present invention are known in the art.

As used herein, the term "composition" is intended to encompass a product comprising the specified ingredients in the specified amounts, as well as any product which results, directly or indirectly, from combinations of the specified ingredients in the specified amounts.

As used herein, the terms "disorder related to FLT3," or "disorders related to FLT3 receptor," or "disorders related to FLT3 receptor tyrosine kinase," or "FLT3 driven cell proliferative disorder" includes diseases associated with or implicating FLT3 activity, for example, mutations leading to constitutive activation of FLT3. Examples of "disorders related to FLT3" include disorders resulting from over stimulation of FLT3 due to mutations in FLT3, or disorders resulting from abnormally high amount of FLT3 activity due to abnormally high number of mutations in FLT3. It is known that over-activity of FLT3 has been implicated in the pathogenesis of many diseases, including the following listed cell proliferative disorders, neoplastic disorders and cancers.

As used herein, the term "cell proliferative disorders" refers to excess cell proliferation of one or more subset of cells in a multicellular organism resulting in harm (i.e., discomfort or decreased life expectancy) to the multicellular organism. Cell proliferative disorders can occur in different types of animals and humans. As used herein, "cell proliferative disorders" include neoplastic disorders.

As used herein, the term "neoplastic disorder" refers to a tumor resulting from abnormal or uncontrolled cellular growth. Examples of neoplastic disorders include, but are not limited to the following disorders, for instance: the myeloproliferative disorders, such as thrombocytopenia, essential thrombocytosis (ET), agnogenic myeloid metaplasia, myelofibrosis (MF), myelofibrosis with myeloid metaplasia (MMM), chronic idiopathic myelofibrosis (UIMF), and polycythemia vera (PV), the cytopenias, and pre-malignant myelodysplastic syndromes; cancers such as glioma cancers, lung cancers, breast cancers, colorectal cancers, prostate cancers, gastric cancers, esophageal cancers, colon cancers, pancreatic cancers, ovarian cancers, and hematological malignancies, including myelodysplasia, multiple myeloma, leukemias, and lymphomas. Examples of hematological malignancies include, for instance, leukemias, lymphomas, Hodgkin's disease, and myeloma. Also, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML, with trilineage myelodysplasia (AMLITMDS), mixed lineage leukemia (MLL), myelodysplastic syndromes (MDSs), myeloproliferative disorders (MPD), and multiple myeloma (MM).

The expression of mutated FLT3, constitutively active FLT3 mutant, and the one or more mutations in an epigenetic regulator gene selected from TET2, IDH1, IDH2, ASXL1, BCOR, SETBP1, or MLL, can be determined using standard molecular biology techniques, including sequencing at the RNA or DNA level, protein expression, protein function, the presence or absence of the RNA, DNA, and/or protein, as will be known to those of skill in the art following the teachings of, e.g., standard techniques for sequencing (including Next Generation Sequencing (NGS)), cloning, RNA and DNA isolation, amplification and purification, detection and identification of chromosomal abnormalities, and various separation techniques are those known and commonly employed by those skilled in the art. A number of standard techniques are described in Sambrook et al. (1989) Molecular Cloning, Second Edition, Cold Spring Harbor Laboratory, Plainview, N.Y.; Maniatis et al. (1982) Molecular Cloning, Cold Spring Harbor Laboratory, Plainview, N.Y.; Wu (ed.) (1993) Meth. Enzymol. 218, Part I; Wu (ed.) (1979) Meth. Enzymol. 68; Wu et al. (eds.) (1983) Meth. Enzymol. 100 and 101; Grossman and Moldave (eds.) Meth. Enzymol. 65; Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley; Schleif and Wensink (1982) Practical Methods in Molecular Biology; Glover (ed.) (1985) DNA Cloning Vol. I and II, IRL Press, Oxford, UK; Hames and Higgins (eds.) (1985) Nucleic Acid Hybridization, IRL Press, Oxford, UK; Setlow and Hollaender (1979) Genetic Engineering: Principles and Methods, Vols. 1-4, Plenum Press, New York; Fitchen, et al. (1993) Annu Rev. Microbiol. 47:739-764; Tolstoshev, et al. (1993) in Genomic Research in Molecular Medicine and Virology, Academic Press; and Ausubel et al. (1992) Current Protocols in Molecular Biology, Greene/Wiley, New York, N.Y. Abbreviations and nomenclature, where employed, are deemed standard in the field and commonly used in professional journals such as those cited herein. The above techniques can be used to detect genetic abnormalities such as aneuploidy, monosomy, trisomy, or polysomy; chromosomal aberrations such as one or more deletions, duplications, translocations, inversions, insertions, rings, or isochromosomes. Additional genetic abnormalities include driver mutations such as those selected from mutations in the epigenetic regulators TET2, IDH1, IDH2, ASXL1, BCOR, SETBP1, or MLL, human or animal, with the names available from Genecards.com, with current accession numbers, sequences, and probes to the same incorporated herein by reference.

For example, detection of gene mutations can be accomplished by detecting nucleic acid molecules (such as DNA)

using nucleic acid amplification methods (such as RT-PCR) or high throughput sequencing (i.e., "next-generation sequencing"). By example, next-generation sequencing platforms such as Illumina may be used to determine the exact genetic sequence of specific genes, or portions of genes, of interest. In brief, DNA from a tumor sample is fragmented, ligated with the appropriate primers and adaptors, and amplified using PCR during "library preparation". The prepared libraries are then sequenced using one of a number of commercially available systems which generates the sequence of the chosen target genes, all exomes, or the entire genome. The sequences are then analyzed using commercially available software, which aligns the tumor sample sequence to the known sequence of the genes of interest and performs a variant calling step, which identifies differences at the DNA level in the tumor sample and determines if such mutations would result in alteration of the amino acid sequence in the translated protein. Using these systems, a person of skill in the art can determine if a subject has one of the identified mutations with in FLT3. Further information on FLT3, including full gene and protein sequences, known clinically relevant variants and mutations, tissue expression, and signaling interaction partners can be found at UniProt (accession number P36888-1), GenBank (accession number NM_04119.2), and GenPept (accession number NP_004110.2).

Driver mutations within TET include frameshift mutations, nonsense mutations, or missense mutations within the catalytic domain. Driver mutations within IDH1 include missense mutations at amino acid residue R132. Driver mutations in IDH2 include missense mutations at amino acid residues R140 or R172. Driver mutations in ASXL1 include frameshift or nonsense mutations. Driver mutations in BCOR include frameshift or nonsense mutations. Driver mutations in SETBP1 include missense mutations in the SKI homologous region between amino acid residues E706 and H917, inclusive. Driver mutations in MLL include PTD mutations and gene fusions. The presence of one or more of these mutations can be determined using standard molecular biology techniques, including Next Generation Sequencing, PCR based tests, or karyotype-based tests (for fusion mutations involving MLL on chromosome 11). Standard analysis methods, including variant calling and such analyses as SIFT (Sorting Intolerant from Tolerant) and PolyPhen (Polymorphism Phenotyping), may be used to determine if a particular variant found in a tumor sample is detrimental to normal protein function. Gene mutation panels such as those used by medical professionals during diagnostic workup of potential proliferative disease patients may also be used. Further information on TET2, including full gene and protein reference sequences and known clinically relevant variants and mutations can be found at UniProt (accession number Q6N021-1), Gen Bank (accession number NM_001127208.2), and GenPept (accession number NP_001120680.1). Further information on IDH1, including full gene and protein reference sequences and known clinically relevant variants and mutations can be found at UniProt (accession number 075874-1), Gen Bank (accession number NM_001282386.1), and GenPept (accession number NP_001269315.1). Further information on IDH2, including full gene and protein reference sequences and known clinically relevant variants and mutations can be found at UniProt (accession number P48735-1), Gen Bank (accession number NM_002159.2), and GenPept (accession number NP_002168.3). Further information on ASXL1, including full gene and protein reference sequences and known clinically relevant variants and mutations can be found at UniProt (accession number Q8IXJ9-1), Gen Bank (accession number NM_015338.5), and GenPept (accession number NP_056153.2). Further information on BCOR, including full gene and protein reference sequences and known clinically relevant variants and mutations can be found at UniProt (accession number Q6W2J9-1), Gen Bank (accession number NM_001123385.1), and GenPept (accession number NP_001116857.1). Further information on SETBP1, including full gene and protein reference sequences and known clinically relevant variants and mutations can be found at UniProt (accession number Q9Y6X0-1), Gen Bank (accession number NM_015559.2), and GenPept (accession number NP_056374.2). Further information on MLL, also known as KMT2A, including full gene and protein reference sequences and known clinically relevant variants and mutations can be found at UniProt (accession number Q03164-1), Gen Bank (accession number NM_005933.3), and GenPept (accession number NP_005924.2).

As used herein, the term "missense mutation" refers to a nucleotide mutation in the DNA sequence which results in an amino acid substitution at the protein level.

As used herein, the term "nonsense mutation" refers to a nucleotide mutation in the DNA sequence which results in an early stop codon. That is, a nucleotide base sequence that signals for the termination of translation, rather than the addition of an amino acid. These mutations results in a truncated protein.

As used herein, the term "frameshift mutation" refers to the insertion or deletion of nucleotides in the DNA sequence that are not a multiple of three. That is, a number of nucleotides are delete or inserted that are not a full codon. This type of mutation shifts the reading frame of the transcript and cannot be translated into a functional protein. For instance, is the non-mutated sequence is AAAGGGTTT, a mutation to AAGGGTTT or AAAAGGGTTT shifts the reading frame, and changes the codons from AAA-GGG-TTT to AAG-GGT-TT or AAA-AGG-GTT-T.

As used herein, the term "fusion" refers to alterations in the genetic sequence, typically as a result of translocation or inversion within a chromosome or between multiple chromosomes, which results in the pairing of part of the MLL gene with a partner gene in the translated protein sequence. For MLL fusions, the resulting translocation is t(11; x), where x is a placeholder for the other chromosome in the translocation.

As used herein, the term "loss-of-function" refers to a mutation that results in a protein that has lost function. Examples include frameshift mutations, nonsense mutations that truncate a catalytic domain or an important binding region necessary for function, and missense mutations within the catalytic or binding domains of certain proteins.

As used herein, the term "gain-of-function" refers to a mutation that results in increased activity of proteins. Examples include the activation ITD or TKD mutations within FLT3, and the PTD mutation in MLL.

As used herein, the term "neomorphic mutation" refers to a mutation that results in a new noncanonical function of the protein, typically corresponding to the loss of the protein's normal function. Examples include R132 mutations in IDH1 and R140 mutations in IDH2.

In a further embodiment, the present invention can be combined with another therapy as a combination therapy for treating or inhibiting the onset of a cell proliferative disorder related to FLT3 in a subject. The combination therapy comprises the administration of a therapeutically effective amount of a compound of the present invention and one or more other anti-cell proliferation therapies including, but not limited to, chemotherapy and radiation therapy.

In an embodiment of the present invention, a compound of the present invention may be administered in combination with chemotherapy. Used herein, chemotherapy refers to a therapy involving a chemotherapeutic agent. A variety of chemotherapeutic agents may be used in combination with the present invention. By way of example only, taxane compounds, specifically, docetaxel, is safely administered in combination with a compound of the present invention in a dosage of 75 mg per square meter ($mg/m^2$) of body surface area.

Chemotherapy is known to those skilled in the art. The appropriate dosage and scheme for chemotherapy will be similar to those already employed in clinical therapies wherein the chemotherapy is delivered in combination with other therapies or used alone.

In another embodiment of the present invention, compounds of the present invention may be administered in combination with radiation therapy. Used herein, "radiation therapy" refers to a therapy that comprises the exposure of a subject in need to radiation. Radiation therapy is known to those skilled in the art. The appropriate dosage and scheme for radiation therapy will be similar to those already employed in clinical therapies wherein the radiation therapy is delivered in combination with other therapies or used alone.

In another embodiment of the present invention, the compounds of the present invention may be administered in combination with a targeted therapy. As used herein, "targeted therapy" refers to a therapy targeting a particular class of proteins involved in tumor development or oncogenic signaling. For example, tyrosine kinase inhibitors against vascular endothelial growth factor have been used in treating cancers.

The present invention also includes methods that include the use of a second pharmaceutical agent in addition to compounds of the present invention, the two may be administered simultaneously or sequentially (in either order).

In one embodiment, the present invention therapeutically effective amounts of the compound having formula I:

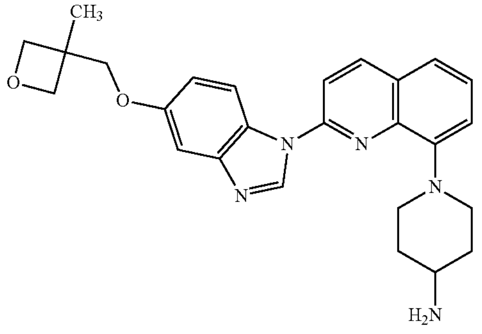 [SMILES: CC1(COc2ccc3c(c2)ncn3-c2ccc3cccc(N4CCC(N)CC4)c3n2)COC1]

or a pharmaceutically acceptable salt or solvate thereof, in a therapeutically or prophylactically effective amount against a proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. Pharmaceutically acceptable salts including hydrochloride, phosphate and lactate are prepared in a manner similar to the benzenesulfonate salt and are well known to those of moderate skill in the art.

Compounds of the present invention may be administered to a subject systemically, for example, orally, intravenously, subcutaneously, intramuscular, intradermal or parenterally. The compounds of the present invention can also be administered to a subject locally.

Compounds of the present invention may be formulated for slow-release or fast-release with the objective of maintaining contact of compounds of the present invention with targeted tissues for a desired range of time.

Compositions suitable for oral administration include solid forms, such as pills, tablets, caplets, capsules, granules, and powders, liquid forms, such as solutions, emulsions, and suspensions. Forms useful for parenteral administration include sterile solutions, emulsions and suspensions.

The daily dosage of the compounds of the present invention may be varied over a wide range from 50 to 500 mg per adult human per day. For oral administration, the compositions are preferably provided in the form of tablets containing 20 and 100 milligrams. The compounds of the present invention may be administered on a regimen up to three times or more per day. Preferably three times per day. Optimal doses to be administered may be determined by those skilled in the art, and will vary with the compound of the present invention used, the mode of administration, the time of administration, the strength of the preparation, the details of the disease condition. Factors associated with patient characteristics, such as age, weight, and diet will call for dosage adjustments.

Preparation of the compounds of the present invention. General synthetic methods which may be referred to for preparing the compounds of formula I are provided in U.S. Pat. No. 5,990,146 (issued Nov. 23, 1999) (Warner-Lambert Co.) and PCT published application numbers WO 99/16755 (published Apr. 8, 1999) (Merck & Co.) WO 01/40217 (published Jul. 7, 2001) (Pfizer, Inc.), US Patent Application No. US 2005/0124599 (Pfizer, Inc.) and U.S. Pat. No. 7,183,414 (Pfizer, Inc.), relevant portions incorporated herein by reference.

Pharmaceutically acceptable salts such as hydrochloride, phosphate and lactate are prepared in a manner similar to the benzenesulfonate salt and are well known to those of moderate skill in the art. The following representative compounds of the present invention are for exemplary purposes only and are in no way meant to limit the invention, including Crenolanib as Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate.

SUMMARY OF EXAMPLES

Example A: The leukemic blasts from a newly diagnosed patient harbored in addition to a FLT3-ITD mutation, a IDH1 R132H mutation, a TET2 3500+1G>A splice site mutation, and a partial tandem duplication mutation in exons 2-8 of MLL (MLL-PTD). The patient achieved reduction in bone marrow blasts to less than 5% following induction chemotherapy followed by sequential administration of crenolanib besylate.

Example B: The leukemic blasts from a newly diagnosed patient harbored in addition to FLT3-ITD and TKD mutations, a IDH2 R140Q mutation, a SRSF2 P95L mutation, and a NPM1 W288fs10+ mutation. The patient achieved reduction in bone marrow blasts to less than 5% following induction chemotherapy followed by sequential administration of crenolanib besylate.

Example C: The leukemic blasts from a newly diagnosed patient harbored in addition to a FLT3-TKD mutation, a partial tandem duplication mutation in exons 2-10 of MLL (MLL-PTD), an ASXL1 frameshift mutation at amino acid residue E635, an ETV6 R378P mutation, a SRSF2 P95H mutation, and a TUSC3 L29F mutation. The patient achieved a reduction in bone marrow blasts to less than 5% following induction chemotherapy followed by sequential administration of crenolanib besylate.

Example D: The leukemic blasts from a newly diagnosed patient harbored in addition to a FLT3-ITD mutation an IDH1 R140Q mutation, and a NPM1 frameshift mutation at amino acid residue W288. The patient achieved reduction in bone marrow blasts to less than 5% following induction chemotherapy followed by sequential administration of crenolanib besylate.

Example E: The leukemic blasts from a newly diagnosed patient harbored in addition to a FLT3-ITD mutation, an IDH1 R132S mutation, a SF3B1 K700E mutation, a RUNX1 frameshift mutation at amino acid residue 5239, and a BCOR frameshift mutation at T477. The patient achieved reduction in bone marrow blasts to less than 5% following induction chemotherapy followed by sequential administration of crenolanib besylate.

Example F: The leukemic blasts from a newly diagnosed patient harbored in addition to a FLT3-TKD mutation, a NRAS G13D mutation, a RUNX1 frameshift mutation at amino acid residue E143, a BCOR nonsense mutation at amino acid Y1350, and a U2AF1 S34F mutation. The patient also had the cytogenetic abnormality trisomy 13. The patient achieved reduction in bone marrow blasts to less than 5% following induction chemotherapy followed by sequential administration of crenolanib besylate.

Example G: The leukemic blasts from a newly diagnosed patient harbored in addition to a FLT3-TKD mutation, a RUNX1 R201Q mutation, a SF3B1 K666T mutation, and a TET2 nonsense mutation at amino acid residue Q939. The patient achieved reduction in bone marrow blasts to less than 5% following induction chemotherapy followed by sequential administration of crenolanib besylate.

Example H: The leukemic blasts from a newly diagnosed patient harbored in addition to a FLT3-ITD mutation, a NPM1 frameshift mutation at amino acid residue W288, and a TET2 frameshift mutation at amino acid residue T606, and the cytogenetic abnormality trisomy 4. The patient achieved reduction in bone marrow blasts to less than 5% following induction chemotherapy followed by sequential administration of crenolanib besylate.

Example I: The leukemic blasts from a relapsed/refractory patient harbored in addition to a FLT3-ITD mutation, a IDH1 R132H mutation, a NPM1 frameshift mutation at amino acid residue W288, a TET2 frameshift mutation at amino acid residue N275, and an ASXL1 A1312V mutation. The patient achieved reduction in bone marrow blasts to less than 5% following salvage chemotherapy followed by sequential administration of crenolanib besylate.

Example J: The leukemic blasts from a relapsed/refractory patient harbored in addition to a FLT3-ITD mutation, a NPM1 frameshift mutation at amino acid residue W288 and a TET2 frameshift mutation at amino acid residue R1440. The patient achieved reduction in bone marrow blasts to less than 5% following salvage chemotherapy followed by sequential administration of crenolanib besylate.

Example K: The leukemic blasts from a relapsed/refractory patient harbored in addition to a FLT3-ITD mutation, a TET2 nonsense mutation at amino acid residue 5420, a U2AF1 S34F mutation, and complex karyotype. The patient achieved reduction in bone marrow blasts to less than 5% following salvage chemotherapy followed by sequential administration of crenolanib besylate.

Example L: The leukemic blasts from a relapsed/refractory patient harbored in addition to a FLT3-TKD mutation, a SETBP1 D866N and G870S mutations, a MLL A53V mutation, a STAG2 K170M mutation, a WT1 frameshift mutation at amino acid residue R158, and a ETV6 frameshift mutation at amino acid residue 1147. The patient achieved reduction in bone marrow blasts to less than 5% following administration of crenolanib besylate.

Example M: The leukemic blasts from a relapsed/refractory patient harbored in addition to FLT3-ITD and TKD mutations, PTPN11 G60R and A72T mutations, NRAS G12C and G13D mutations, a BCOR frameshift mutation at amino acid residue R1197, a WT1 frameshift at amino acid reside A365, a RUNX1 frameshift mutation at amino acid residue Q308, and a SF3B1 N626D mutation. The patient achieved reduction in bone marrow blasts to less than 5% following administration of crenolanib besylate.

Example N: The leukemic blasts from a relapsed/refractory pediatric patient harbored in addition to a FLT3-A848P mutation, an MLL-MLLT3 fusion mutation. The patient achieved reduction in bone marrow blasts to less than 5% following treatment with salvage chemotherapy followed by sequential administration of crenolanib besylate.

Example O: The leukemic blasts from a relapsed/refractory pediatric patient harbored in addition to FLT3 D385E and D835H mutations, an MLL-ELL fusion mutation. The patient achieved reduction in bone marrow blasts from 60% to 15%, classified as a partial response, following treatment with crenolanib.

Newly Diagnosed AML—Examples

Example A: The effect of crenolanib besylate therapy in a newly diagnosed AML patient with FLT3-ITD, IDH1, TET2, and MLL mutations: achievement of reduction in bone marrow blasts to less than 5% with hematologic recovery.

A 55-year-old male was diagnosed with AML positive for a FLT3-ITD mutation. The patient's leukemic blasts also carried mutations in the IDH1, TET2, and MLL genes. Specifically, the patient had an IDH1 R132H missense mutation, a TET2 splice site mutation (3500+1G>A), and an MLL-PTD mutation. As these mutations are characterized as independent driver mutations, and are each associated with a particularly poor prognosis, the patient's presentation of these mutations placed him in a significantly high-risk group for AML patients, associated with poor response rates, increased cumulative incidence of relapse, and shortened survival. Half of patients with FLT3-ITD and IDH1 co-occurring mutations are expected to die within 1.5 years of diagnosis. (Boddu et al., 2017). Half of patients with TET2 mutations are expected to die within approximately 1.5 years of diagnosis, with patients with co-occurring FLT3 mutations having an even worse median survival. (Aslanyan et al., 2014). Half of patients with FLT3 mutations and MLL-PTD mutations are expected to die within 1 year. (Papaemmanuil et al., 2016).

At diagnosis, the patient was found to have 91% bone marrow blasts. Following diagnosis, the patient was provided with oral crenolanib besylate on a clinical trial for newly diagnosed AML (NCT02283177). The patient was initially treated with induction chemotherapy, comprised of seven days of cytarabine and three days of idarubicin. The patient began therapy with 100 mg of crenolanib besylate three times daily on day 10.

A bone marrow biopsy taken on day 15 of the clinical trial revealed the patient's bone marrow blasts had reduced to less than 5%, classified as a complete remission. An additional bone marrow biopsy taken on day 31 of induction treatment confirmed complete remission, and the patient received a hematopoietic stem cell transplant. The patient's overall survival was greater than 2 years, significantly longer than the median overall survival for patients with FLT3-ITD, IDH1, TET2, and MLL co-occurring mutations in the literature.

Table 1 below illustrates the ability of crenolanib to clear and maintain clearance of malignant leukemia in the bone marrow of Example A, a newly diagnosed patient with FLT3-ITD, IDH1, TET2, and MLL mutations after treatment with chemotherapy and crenolanib besylate.

| Days on Clinical Trial | Bone Marrow Blast (%) |
|---|---|
| 0 | 91% |
| 15 | <5% |
| 31 | <5% |
| 70 | <5% |
| 176 | <5% |

Example B: The effect of crenolanib besylate therapy in a newly diagnosed AML patient with FLT3-ITD, FLT3-TKD, IDH2, SRSF2, and NPM1 mutations: achievement of reduction in bone marrow blasts to less than 5% with hematologic recovery.

A 54-year-old female was diagnosed with AML positive for both FLT3-ITD and FLT3-TKD mutations. The patient's leukemic blasts also had mutations in the IDH2, SRSF2, and NPM1 genes. Specifically, the patient had an IDH2 R140Q missense mutation, a SRSF2 P95L, and a NPM1 frameshift mutation at amino acid residue W288. As these mutations are characterized as independent driver mutations, and are associated with a particularly poor prognosis, the patient's presentation of these co-occurring mutations placed her in a significantly high-risk group for AML patients, associated with poor response rates, increased cumulative incidence of relapse, and shortened survival. Half of patients with FLT3-ITD and IDH1 co-occurring mutations are expected to die within 1.5 years of diagnosis. (Boddu et al., 2017). Half of patients with SRSF2 mutations are expected to die within 1.2 years. (Hou et al., 2016). While NPM1 mutations alone are a favorable prognostic factor according to ELN guidelines, when present in combination with FLT3-ITD mutations, it is a poor prognostic marker. (Dohner et al., 2017).

At diagnosis, the patient was found to have 95% bone marrow blasts. Following diagnosis, the patient was provided with oral crenolanib besylate on a clinical trial for newly diagnosed AML patients (NCT02283177). The patient was initially treated with induction chemotherapy, comprised of seven days of cytarabine and three days of idarubicin. The patient began therapy with 100 mg of crenolanib besylate three times daily on day 12.

A bone marrow biopsy taken on day 14 of the clinical trial revealed the patient's bone marrow blasts had reduced to less than 5%, classified as a complete remission. An additional bone marrow biopsy taken on day 27 of induction treatment confirmed complete remission. The patient remains alive and free of disease more than 5 years after start of therapy, significantly longer than the expected median survival for patients with these co-occurring mutations.

Table 2 below illustrates the ability of crenolanib to clear and maintain clearance of malignant leukemia in the bone marrow of Example B, a newly diagnosed AML patient with FLT3-ITD, FLT3-TKD, IDH1, SRSF2, and NPM1 mutations after treatment with chemotherapy and crenolanib besylate.

| Days on Clinical Trial | Bone Marrow Blast (%) |
|---|---|
| 0 | 95% |
| 14 | <5% |
| 27 | <5% |
| 147 | <5% |
| 217 | <5% |

Example C: The effect of crenolanib besylate therapy in a newly diagnosed AML patient with FLT3-TKD, MLL, ASXL1, ETV6, SRSF2, and TUSC3 mutations: achievement of reduction in bone marrow blasts to less than 5% with hematologic recovery.

A 69-year-old male was diagnosed with AML positive for a FLT3-TKD mutation. The patient's leukemic blasts also carried mutations in the MLL, ASXL1, ETV6, SRSF2, and TUSC3 genes. Specifically, the patient had a partial tandem duplication mutation in exons 2-10 of MLL (MLL-PTD), an ASXL1 frameshift mutation at amino acid residue E635, an ETV6 R378P mutation, a SRSF2 P95H mutation, and a TUSC3 L29F mutation. As these mutations are characterized as independent driver mutations, and are each associated with a particularly poor prognosis, the patient's presentation of these mutations placed him in a significantly high-risk group for AML patients, associated with poor response rates, increased cumulative incidence of relapse, and shortened survival. Less than half of patients with ASXL1 mutations are expected to survive 16 months. (Prat-corona et al., 2012). Half of patients with SRSF2 mutations are expected to die within 1.2 years. (Hou et al., 2016). While ETV6 mutations are less common in AML and have not been investigated at the detail necessary to derive expected survival as the population is small, it has previously been shown that patients with more than four independent driving mutations have significantly worse prognosis than patients with fewer driver mutations. (Papaemmanuil et al., 2016). Half of newly diagnosed patients with 5 to 6 separate driver mutations are expected to die within 2 years of diagnosis. (Papaemmanuil et al., 2016).

At diagnosis, the patient was found to have 18% bone marrow blasts and had previously been diagnosed with myeloproliferative neoplasm approximately 1.5 years prior to developing AML for which he received treatment. Patients with secondary AML following an antecedent hematological disorder have poor outcomes compared to patients with de novo AML, with half of patients older than 60 years of age with secondary AML that received treatment for the antecedent hematological disorder having an expected median overall survival of only 4.7 months. Following diagnosis, the patient was provided with oral crenolanib besylate on a clinical trial for newly diagnosed AML (NCT02283177). The patient was initially treated with induction chemotherapy, comprised of seven days of cytarabine and three days of idarubicin. The patient began therapy with 100 mg of crenolanib besylate three times daily on day 10.

A bone marrow biopsy taken on day 38 of treatment revealed the patient's bone marrow blasts had reduced to less than 5%, with full neutrophil recovery and partial platelet recovery, classified as a complete remission with partial hematologic recovery. The patient's overall survival was greater than 15 months, longer than the expected median overall survival for patients with secondary AML.

Table 3 below illustrates the ability of crenolanib to clear and maintain clearance of malignant leukemia in the bone marrow of Example C, a newly diagnosed patient with FLT3-TKD, MLL, ASXL1, ETV6, SRSF2, and TUSC3 mutations after treatment with chemotherapy and crenolanib besylate.

| Days on Clinical Trial | Bone Marrow Blast (%) |
|---|---|
| 0 | 18% |
| 38 | <5% |

Example D: The effect of crenolanib besylate therapy in a newly diagnosed AML patient with FLT3-ITD, IDH1, and NPM1 mutations: achievement of reduction in bone marrow blasts to less than 5% with hematologic recovery.

A 58-year-old female was diagnosed with AML positive for a FLT3-ITD mutation. The patient's leukemic blasts also carried mutations in the IDH1 and NPM1 genes. Specifically, the patient had an IDH1 R140Q mutation, and a NPM1 mutation at amino acid residue W288. As these mutations are characterized as independent driver mutations, and are each associated with a particularly poor prognosis, the patient's presentation of these mutations placed him in a significantly high-risk group for AML patients, associated with poor response rates, increased cumulative incidence of relapse, and shortened survival. Half of patients with FLT3-ITD and IDH1 co-occurring mutations are expected to die within 1.5 years of diagnosis. (Boddu et al., 2017). While NPM1 mutations alone are a favorable prognostic factor according to ELN guidelines, when present in combination with FLT3-ITD mutations, it is a poor prognostic marker. (Dohner et al., 2017).

At diagnosis, the patient was found to have 83% bone marrow blasts. Following diagnosis, the patient was provided with oral crenolanib besylate on a clinical trial for newly diagnosed AML (NCT02283177). The patient was initially treated with induction chemotherapy, comprised of seven days of cytarabine and three days of daunorubicin. The patient began therapy with 100 mg of crenolanib besylate three times daily on day 10.

A bone marrow biopsy taken on day 21 of the clinical trial revealed the patient's bone marrow blasts had reduced to less than 5%, classified as a complete remission. Additional bone marrow biopsies taken on days 36, 76, 124, and 455 confirmed the patient remained in remission. The patient remains alive and in remission 4 years after initial treatment.

Table 4 below illustrates the ability of crenolanib to clear and maintain clearance of malignant leukemia in the bone marrow of Example D, a newly diagnosed patient with FLT3-ITD, IDH1, and NPM1 mutations after treatment with chemotherapy and crenolanib besylate.

| Days on Clinical Trial | Bone Marrow Blast (%) |
|---|---|
| 0 | 83% |
| 36 | <5% |
| 76 | <5% |
| 124 | <5% |
| 455 | <5% |

Example E: The effect of crenolanib besylate therapy in a newly diagnosed AML patient with FLT3-ITD, IDH1, SF3B1, RUNX1, and BCOR mutations: achievement of reduction in bone marrow blasts to less than 5% with hematologic recovery.

A 68-year-old male was diagnosed with AML positive for a FLT3-ITD mutation. The patient's leukemic blasts also carried mutations in the IDH1, SF3B1, RUNX1, and BCOR genes. Specifically, the patient had an IDH1 R132S mutation, a SF3B1 K700E mutation, a RUNX1 frameshift mutation at amino acid residue 5239, and a BCOR frameshift mutation at T477. As these mutations are characterized as independent driver mutations, and are each associated with a particularly poor prognosis, the patient's presentation of these mutations placed him in a significantly high-risk group for AML patients, associated with poor response rates, increased cumulative incidence of relapse, and shortened survival. Half of patients with FLT3-ITD and IDH1 co-occurring mutations are expected to die within 1.5 years of diagnosis. (Boddu et al., 2017). Half of patients with SF3B1 mutations are expected to die within 4.5 months. (Hou et al., 2016). Half of patients with RUNX1 mutations are expected to die within 10 months, with only 2% of patients surviving at 5 years. (Mendler et al., 2012). Half of patients with BCOR mutations die within approximately 2 years. (Zhang et al., 2020). Half of newly diagnosed patients with 5 to 6 separate driver mutations are expected to die within 2 years of diagnosis. (Papaemmanuil et al., 2016).

At diagnosis, the patient was found to have 93% bone marrow blasts. Following diagnosis, the patient was provided with oral crenolanib besylate on a clinical trial for newly diagnosed AML (NCT02283177). The patient was initially treated with induction chemotherapy, comprised of seven days of cytarabine and three days of daunorubicin. The patient began therapy with 100 mg of crenolanib besylate three times daily on day 10.

A bone marrow biopsy taken on day 22 of the clinical trial revealed the patient's bone marrow blasts had reduced to 49%. At this point, the patient received a second round of induction chemotherapy followed by crenolanib besylate (re-induction). On day 48 of the clinical trial, a bone marrow biopsy showed <5% blasts, classified as complete remission. Additional bone marrow biopsies taken on days 118, 232, and 321 showed the patient remained in remission. The patient remains alive and in remission 4 years after diagnosis, significantly exceeding the expected survival for patients with IDH1, SF3B1, and RUNX1 mutations.

Table 5 below illustrates the ability of crenolanib to clear and maintain clearance of malignant leukemic blasts in the bone marrow of Example E, a newly diagnosed patient with FLT3-ITD, IDH1, SF3B1, RUNX1, and BCOR mutations after treatment with chemotherapy and crenolanib besylate.

| Days on Clinical Trial | Bone Marrow Blast (%) |
|---|---|
| 0 | 91% |
| 22 | <5% |

-continued

| Days on Clinical Trial | Bone Marrow Blast (%) |
|---|---|
| 48 | <5% |
| 118 | <5% |
| 232 | <5% |
| 321 | <5% |

Example F: The effect of crenolanib besylate therapy in a newly diagnosed AML patient with FLT3-TKD, NRAS, RUNX1, BCOR, and U2AF1 mutations and trisomy 13: achievement of reduction in bone marrow blasts to less than 5% with hematologic recovery.

A 59-year-old male was diagnosed with AML positive for FLT3-TKD mutation. The patient's leukemic blasts also carried mutations in NRAS, RUNX1, BCOR, and U2AF1 as well as the cytogenetic abnormality trisomy 13. Specifically, the patient had a NRAS G13D mutation, a RUNX1 frameshift mutation at amino acid residue E143, a BCOR nonsense mutation at amino acid Y1350, and a U2AF1 S34F mutation. As these mutations are characterized as independent driver mutations, and each are associated with a particularly poor prognosis, the patient's presentation of these mutations placed him in a significantly high-risk group for AML patients, associated with poor response rates, increased cumulative incidence of relapse, and shortened survival. Half of patients with NRAS mutations are expected to die within 1 year of diagnosis. (Ball et al., 2019). Half of patients with RUNX1 mutations are expected to die within 10 months, with only 2% of patients surviving at 5 years. (Mendler et al., 2012). Half of patients with BCOR mutations die within approximately 2 years. (Zhang et al., 2020). Half of patients with U2AF1 mutations are expected to die within 2 months of diagnosis. (Hou et al., 2016). Half of patients with trisomy 13 are expected to die within 9 months of diagnosis. (Herold et al., 2014). Half of newly diagnosed patients with 5 to 6 separate driver mutations are expected to die within 2 years of diagnosis. (Papaemmanuil et al., 2016).

At diagnosis, the patient was found to have 70% bone marrow blasts. Following diagnosis, the patient was provided with oral crenolanib besylate on a clinical trial for newly diagnosed AML (NCT02283177). The patient was initially treated with induction chemotherapy, comprised of seven days of cytarabine and three days of idarubicin. The patient began therapy with 100 mg of crenolanib besylate three times daily on day 9.

A bone marrow biopsy taken on day 28 of the clinical trial revealed the patient's bone marrow blasts had reduced to 8%, classified as a partial remission. The patient received a second cycle of induction chemotherapy and on day 90 of the clinical trial a bone marrow biopsy revealed the patient's bone marrow blasts had reduced to less than 5%, classified as a complete remission. The patient remained alive 1.8 years after starting therapy, the last point of follow-up for this patient.

Table 6 below illustrates the ability of crenolanib to clear and maintain clearance of malignant leukemia in the bone marrow of Example F, a newly diagnosed patient with FLT3-TKD, NRAS, RUNX1, BCOR, and U2AF1 mutations as well as trisomy 13 after treatment with chemotherapy and crenolanib besylate.

| Days on Clinical Trial | Bone Marrow Blast (%) |
|---|---|
| 0 | 70% |
| 28 | 8% |
| 90 | <5% |

Example G: The effect of crenolanib besylate therapy in a newly diagnosed AML patient with FLT3-TKD, RUNX1, SF3B1, and TET2 mutations: achievement of reduction in bone marrow blasts to less than 5% with hematologic recovery.

A 68-year-old female was diagnosed with AML positive for a FLT3-TKD mutation. The patient's leukemic blasts also carried mutations in the RUNX1, SF3B1, and TET2 genes. Specifically, the patient had a RUNX1 R201Q mutation, a SF3B1 K666T mutation, and a TET2 nonsense mutation at amino acid residue Q939. As these mutations are characterized as independent driver mutations, and are each associated with a particularly poor prognosis, the patient's presentation of these mutations placed him in a significantly high-risk group for AML patients, associated with poor response rates, increased cumulative incidence of relapse, and shortened survival. Half of patients with RUNX1 mutations are expected to die within 10 months, with only 2% of patients surviving at 5 years. (Mendler et al., 2012). Half of patients with SF3B1 mutations are expected to die within 4.5 months. (Hou et al., 2016). Half of patients with TET2 mutations are expected to die within approximately 1.5 years of diagnosis, with patients with co-occurring FLT3 mutations having an even worse median survival. (Aslanyan et al., 2014).

At diagnosis, the patient was found to have 54% bone marrow blasts. Following diagnosis, the patient was provided with oral crenolanib besylate on a clinical trial for newly diagnosed AML (NCT02283177). The patient was initially treated with induction chemotherapy, comprised of seven days of cytarabine and three days of daunorubicin. The patient began therapy with 100 mg of crenolanib besylate three times daily on day 9.

A bone marrow biopsy taken on day 21 of the clinical trial revealed the patient's bone marrow blasts had reduced to less than 5%, classified as a complete remission. Additional bone marrow biopsies taken on days 33, 162, and 217 showed the patient remained in remission. The patient's overall survival was 3.3 years, significantly longer than the median overall survival expected for patients with FLT3-TKD, RUNX1, SF3B1, and TET2 mutations.

Table 7 below illustrates the ability of crenolanib to clear and maintain clearance of malignant leukemia in the bone marrow of Example G, a newly diagnosed patient with FLT3-TKD, RUNX1, SF3B1, and TET2 mutations after treatment with chemotherapy and crenolanib besylate.

| Days on Clinical Trial | Bone Marrow Blast (%) |
|---|---|
| 0 | 54% |
| 21 | <5% |
| 33 | <5% |
| 162 | <5% |
| 217 | <5% |

Example H: The effect of crenolanib besylate therapy in a newly diagnosed AML patient with FLT3-ITD, NPM1 and TET2 mutations and trisomy 4: achievement of reduction in bone marrow blasts to less than 5% with hematologic recovery.

A 70-year-old male was diagnosed with AML positive for a FLT3-ITD mutation. The patient's leukemic blasts also carried mutations in the NPM1 and TET2 genes as well as the cytogenetic abnormality trisomy 4. Specifically, the patient had a NPM1 frameshift mutation at amino acid residue W288 and a TET2 frameshift mutation at amino acid residue T606. As these mutations are characterized as independent driver mutations, and are each associated with a particularly poor prognosis, the patient's presentation of these mutations placed him in a significantly high-risk group for AML patients, associated with poor response rates, increased cumulative incidence of relapse, and shortened survival. While NPM1 mutations alone are a favorable prognostic factor according to ELN guidelines, when present in combination with FLT3-ITD mutations, it is a poor prognostic marker. (Dohner et al., 2017). Half of patients with TET2 mutations are expected to die within approximately 1.5 years of diagnosis, with patients with co-occurring FLT3 mutations having an even worse median survival. (Aslanyan et al., 2014). Half of patients with trisomy 4 are expected to die within 2 years of diagnosis. (Chilton, Hills, Burnett, & Harrison, 2016).

At diagnosis, the patient was found to have 93% bone marrow blasts. Following diagnosis, the patient was provided with oral crenolanib besylate on a clinical trial for newly diagnosed AML (NCT02283177). The patient was initially treated with induction chemotherapy, comprised of seven days of cytarabine and three days of daunorubicin. The patient began therapy with 100 mg of crenolanib besylate three times daily on day 9.

A bone marrow biopsy taken on day 35 of the clinical trial revealed the patient's bone marrow blasts had reduced to less than 5%, classified as a complete remission. Additional bone marrow biopsies taken on days 82 and 197 confirmed the patient remained in remission and the patient received a bone marrow transplant. The patient remains alive and in remission 4 years after diagnosis, significantly exceeding the expected median survival for patients with FLT3-ITD, NPM1, and TET2 mutations and trisomy 4.

Table 8 below illustrates the ability of crenolanib to clear and maintain clearance of malignant leukemia in the bone marrow of Example H, a newly diagnosed patient with FLT3-ITD, NPM1, and TET2 mutations and trisomy 4 after treatment with chemotherapy and crenolanib besylate.

| Days on Clinical Trial | Bone Marrow Blast (%) |
|---|---|
| 0 | 93% |
| 35 | <5% |
| 82 | <5% |
| 197 | <5% |

Example I: The effect of crenolanib besylate therapy in a relapsed/refractory AML patient with FLT3-ITD, IDH1, NPM1, TET2, and ASXL1 mutations and complex karyotype: achievement of reduction in bone marrow blasts to less than 5% with hematologic recovery.

A 73-year-old male was diagnosed with relapsed AML positive for a FLT3-ITD mutation. Molecular testing performed at second relapse revealed the patient had a FLT3-ITD mutation. The patient's leukemic blasts also carried mutations in the IDH1, NPM1, TET2, and ASXL1 genes. Specifically, the patient had a IDH1 R132H mutation, a NPM1 frameshift mutation at amino acid residue W288, a TET2 frameshift mutation at amino acid residue N275, and an ASXL1 A1312V mutation. As these mutations are characterized as independent driver mutations, and are each associated with a particularly poor prognosis, the patient's presentation of these mutations placed him in a significantly high-risk group for AML patients, associated with poor response rates, increased cumulative incidence of relapse, and shortened survival. While NPM1 mutations alone are a favorable prognostic factor according to ELN guidelines, when present in combination with FLT3-ITD mutations, it is a poor prognostic marker. (Dohner et al., 2017). Half of newly diagnosed patients with TET2 mutations are expected to die within approximately 1.5 years of diagnosis, with patients with co-occurring FLT3 mutations having an even worse median survival. (Aslanyan et al., 2014). Less than half of newly diagnosed patients with ASXL1 mutations are expected to survive 16 months. (Pratcorona et al., 2012). Half of newly diagnosed patients with 5 to 6 separate driver mutations are expected to die within 2 years of diagnosis. (Papaemmanuil et al., 2016). For all mutation groups, the prognosis of relapsed/refractory patients is significantly worse than for newly diagnosed patients.

Following his diagnosis, the patient was initially treated with Vyxeos, a liposomal formulation of induction chemotherapy agents and achieved remission. Approximately two years later, the patient relapsed and was treated with salvage chemotherapy comprised of clofarabine, idarubicin, and cytarabine, again achieving a complete remission. Approximately four years after second remission, the patient unfortunately once again relapsed and was provided with oral crenolanib besylate on a clinical trial for relapsed/refractory AML patients (NCT02400281). The patient was initially treated with salvage chemotherapy, comprised of four days of cytarabine and three days of idarubicin. The patient began therapy with 100 mg of crenolanib besylate three times daily on day 5. At study entry, the patient was found to have 95% bone marrow blasts.

A bone marrow biopsy taken on day 24 of the clinical trial revealed the patient's bone marrow blasts had reduced to less than 5%, classified as a complete remission. The patient continued to receive single agent crenolanib as maintenance therapy for one year. Due to the patient's advanced age, no further bone marrow biopsies were performed on study as the patient showed no signs of relapse, such as circulating blasts. The patient's overall survival from study enrollment exceeded 2 years (at which point the patient was no longer followed per the study protocol), significantly exceeding the expected survival for relapsed/refractory AML patients with FLT3-ITD, NPM1, TET2, and ASXL1 mutations.

Table 9 below illustrates the ability of crenolanib to clear malignant leukemia in the bone marrow of Example I, a relapsed/refractory patient with FLT3-ITD, NPM1, TET2, and ASXL1 mutations.

| Days on Clinical Trial | Bone Marrow Blast (%) |
|---|---|
| 0 | 95% |
| 24 | <5% |

Example J: The effect of crenolanib besylate therapy in a relapsed/refractory AML patient with FLT3-ITD a NPM1, and TET2 mutations: achievement of reduction in bone marrow blasts to less than 5% with hematologic recovery.

A 60-year-old female was diagnosed with refractory AML positive for a FLT3-ITD mutation. The patient's leukemic blasts also carried mutations in the NPM1 and TET2 genes. Specifically, the patient had a NPM1 frameshift mutation at amino acid residue W288 and a TET2 frameshift mutation at amino acid residue R1440. As these mutations are characterized as independent driver mutations, and are each associated with a particularly poor prognosis, the patient's presentation of these mutations placed her in a significantly high-risk group for AML patients, associated with poor response rates, increased cumulative incidence of relapse, and shortened survival. While NPM1 mutations alone are a favorable prognostic factor according to ELN guidelines, when present in combination with FLT3-ITD mutations, it is a poor prognostic marker. (Dohner et al., 2017). Half of newly diagnosed patients with TET2 mutations are expected to die within approximately 1.5 years of diagnosis, with patients with co-occurring FLT3 mutations having an even worse median survival. (Aslanyan et al., 2014). For all mutation groups, the prognosis of relapsed/refractory patients is significantly worse than for the newly diagnosed patients cited herein.

Following her initial AML diagnosis, the patient was treated with induction chemotherapy comprised of cytarabine and idarubicin but did not respond. The patient was then provided with oral crenolanib besylate on a clinical trial for relapsed/refractory AML patients (NCT02400281). The patient was initially treated with salvage chemotherapy, comprised of five days of fludarabine and cytarabine, three days of idarubicin, and one day of granulocyte colony stimulating factor. The patient began therapy with 100 mg of crenolanib besylate three times daily on day 6. At study entry, the patient was found to have 54% bone marrow blasts.

A bone marrow biopsy taken on day 26 of the clinical trial revealed the patient's bone marrow blasts had reduced to less than 5%, classified as a complete remission. A second bone marrow biopsy taken on day 40 confirmed the patient remained in remission and the patient received a hematopoietic stem cell transplant. The patient's survival exceeded 10 months after study enrollment.

Table 10 below illustrates the ability of crenolanib to clear malignant leukemia in the bone marrow of Example J, a relapsed/refractory patient with FLT3-ITD, NPM1, and TET2 mutations.

| Days on Clinical Trial | Bone Marrow Blast (%) |
|---|---|
| 0 | 54% |
| 26 | <5% |
| 40 | <5% |

Example K: The effect of crenolanib besylate therapy in a relapsed/refractory AML patient with FLT3-ITD, TET2, and U2AF1 mutations and complex karyotype: achievement of reduction in bone marrow blasts to less than 5% with hematologic recovery.

A 74-year-old male was diagnosed with relapsed AML positive for a FLT3-ITD mutation. The patient's leukemic blasts also harbored mutations in the TET2 and U2AF1 genes as well as a complex karyotype. Specifically, the patient had a TET2 nonsense mutation at amino acid residue 5420 and a U2AF1 S34F mutation. As these mutations are characterized as independent driver mutations, and are each associated with a particularly poor prognosis, the patient's presentation of these mutations placed him in a significantly high-risk group for AML patients, associated with poor response rates, increased cumulative incidence of relapse, and shortened survival. Half of newly diagnosed patients with TET2 mutations are expected to die within approximately 1.5 years of diagnosis, with patients with co-occurring FLT3 mutations having an even worse median survival. (Aslanyan et al., 2014). Half of patients with U2AF1 mutations are expected to die within 2 months of diagnosis. (Hou et al., 2016). Half of patients with a complex karyotype are expected to die within 2 years of diagnosis. (Papaemmanuil et al., 2016). For all mutation groups, the prognosis of relapsed/refractory patients is significantly worse than for newly diagnosed patients.

Following his diagnosis, the patient was treated with induction chemotherapy and achieved remission. Approximately 6 months later, the patient relapsed and was provided with oral crenolanib besylate on a clinical trial for relapsed/refractory AML patients (NCT02626338). The patient was initially treated with salvage chemotherapy, comprised of six days of cytarabine and three days of mitoxantrone. The patient began therapy with 100 mg of crenolanib besylate three times daily on day 8. At study entry, the patient was found to have 57% bone marrow blasts.

A bone marrow biopsy taken on 35 of the clinical trial revealed the patient's bone marrow blasts had reduced to less than 5%, classified as a complete remission. A second bone marrow biopsy taken on day 52 confirmed the patient remained in remission. At this time, the patient had completed the study, per protocol. The patient died in remission 6 months after study entry due to age-related conditions.

Table 11 below illustrates the ability of crenolanib to clear malignant leukemia in the bone marrow of Example K, a relapsed/refractory patient with FLT3-ITD, TET2, and U2FAF1 mutations and complex karyotype.

| Days on Clinical Trial | Bone Marrow Blast (%) |
|---|---|
| 0 | 57% |
| 35 | <5% |
| 52 | <5% |

Example L: The effect of crenolanib besylate therapy in a relapsed/refractory AML patient with FLT3-TKD, SETBP1, MLL, STAG2, WT1, and ETV6 mutations: achievement of reduction in bone marrow blasts to less than 5% with hematologic recovery.

A 52-year-old female was diagnosed with relapsed AML positive for a FLT3-TKD mutation. The patient's leukemic blasts also harbored mutations in the SETBP1, MLL, STAG2, WT1, and ETV6 genes. Specifically, the patient had a SETBP1 D866N and G870S mutations, a MLL A53V mutation, a STAG2 K170M mutation, a WT1 frameshift mutation at amino acid residue R158, and a ETV6 frameshift mutation at amino acid residue 1147. As these mutations are characterized as independent driver mutations, and are each associated with a particularly poor prognosis, the patient's presentation of these mutations placed her in a significantly high-risk group for AML patients, associated with poor response rates, increased cumulative incidence of relapse, and shortened survival. Half of newly diagnosed older patients (>60 years of age) with SETBP1 mutations are expected to die within 3 months of diagnosis. (Cristobal et al., 2010) Half of newly diagnosed patients with chromatin-spliceosome mutations, including STAG2, are expected to die within 1 year of diagnosis. (Papaemmanuil et al., 2016). Half of newly diagnosed patients with WT1 mutations are expected to die within 1 year of diagnosis, with less than 15% of patients expected to survive more than 2 years. (Paschka et al., 2008). Half of newly diagnosed patients with 5 to 6 separate driver mutations are expected to die within 2 years of diagnosis. (Papaemmanuil et al., 2016). For all mutation groups, the prognosis of relapsed/refractory patients is significantly worse than for newly diagnosed patients.

Following her initial diagnosis, the patient was treated with induction chemotherapy and achieved remission. Approximately 10 months later, the patient relapsed and was treated with guadecitabine, a hypomethylating agent, as salvage therapy, once again achieving remission. Eight months later, the patient relapsed for a second time and was provided with single agent crenolanib besylate at 100 mg three times daily on a clinical trial for relapsed/refractory AML patients (NCT01657682). At study enrollment, the patient had 7% bone marrow blasts.

A bone marrow biopsy taken on day 27 of the clinical trial revealed the patient's bone marrow blasts had reduced to less than 5%, classified as a complete remission without platelet recovery. Unfortunately, financial and insurance issues interrupted the patient's treatment with the study institution, and the patient was lost to follow-up after completing 50 days of single agent crenolanib besylate therapy.

Table 12 below illustrates the ability of crenolanib to clear malignant leukemia in the bone marrow of Example L, a relapsed/refractory patient with FLT3-TKD, SETBP1, MLL, STAG2, WT1, and ETV6 mutations.

| Days on Clinical Trial | Bone Marrow Blast (%) |
|---|---|
| 0 | 7% |
| 27 | <5% |

Example M: The effect of crenolanib besylate therapy in a relapsed/refractory AML patient with FLT3-ITD, FLT3-TKD, PTPN11, NRAS, BCOR, WT1, RUNX1, and SF3B1 mutations: achievement of reduction in bone marrow blasts to less than 5% with hematologic recovery.

A 65-year-old male was diagnosed with relapsed AML positive for FLT3-ITD and TKD mutations. The patient's leukemic blasts also harbored mutations in the PTPN11, NRAS, BCOR, WT1, RUNX1, and SF3B1 genes. As these mutations are characterized as independent driver mutations, and are each associated with a particularly poor prognosis, the patient's presentation of these mutations placed him in a significantly high-risk group for AML patients, associated with poor response rates, increased cumulative incidence of relapse, and shortened survival. Half of newly diagnosed patients with PTPN11 mutations die within 9 months of diagnosis. (Kaner et al., 2018). Half of newly diagnosed patients with NRAS mutations are expected to die within 1 year of diagnosis. (Ball et al., 2019) Half of newly diagnosed patients with BCOR mutations die within approximately 2 years. (Zhang et al., 2020). Half of newly diagnosed patients with WT1 mutations are expected to die within 1 year of diagnosis, with less than 15% of patients expected to survive more than 2 years. (Paschka et al., 2008). Half of newly diagnosed patients with RUNX1 mutations are expected to die within 10 months, with only 2% of patients surviving at 5 years. (Mendler et al., 2012). Half of newly diagnosed patients with SF3B1 mutations are expected to die within 4.5 months. (Hou et al., 2016). Half of newly diagnosed patients with 7 or more separate driver mutations are expected to die within 6 months of diagnosis. (Papaemmanuil et al., 2016). For all mutation groups, the prognosis of relapsed/refractory patients is significantly worse than for newly diagnosed patients.

Following his initial diagnosis, the patent was treated with induction chemotherapy, but was refractory to treatment. After 2 cycles of chemotherapy failed to achieve remission, the patient was administered azacitidine in combination with the FLT3 tyrosine kinase inhibitor quizartinib, achieving remission. Approximately 4 months after remission, the patient relapsed and was provided with single agent crenolanib besylate at 100 mg three times daily on a clinical trial for relapsed/refractory AML patients (NCT01657682). At study entry the patient had 12% bone marrow blasts.

A bone marrow biopsy taken on day 28 of the clinical trial revealed the patient's bone marrow blasts had reduced to less than 5%, classified as a complete remission with partial hematologic recovery. Additional biopsies taken on days 153 and 175 of the clinical trial confirmed the patient remained in remission. On day 205 of the clinical trial, the patient chose to travel internationally and unfortunately died in remission of septicemia. The patient's overall survival exceeded 7.5 months, significantly longer than the median survival expected for relapsed/refractory patients with FLT3-ITD, FLT3-TKD, PTPN11, NRAS, BCOR, WT1, RUNX1, and SF3B1 mutations.

Table 13 below illustrates the ability of crenolanib to clear malignant leukemia in the bone marrow of Example M, a relapsed/refractory patient with FLT3-ITD, FLT3-TKD, PTPN11, NRAS, BCOR, WT1, RUNX1, and SF3B1 mutations who relapsed after receiving the FLT3 tyrosine kinase inhibitor quizartinib.

| Days on Clinical Trial | Bone Marrow Blast (%) |
|---|---|
| 0 | 12% |
| 28 | <5% |
| 153 | <5% |
| 205 | <5% |

Example N: The effect of crenolanib besylate therapy in a relapsed/refractory pediatric AML patient with FLT3-TKD and MLL fusion mutations: achievement of reduction in bone marrow blasts to less than 5% with hematologic recovery.

A 4-year-old male was diagnosed with relapsed AML positive for a FLT3-A848P mutation. The patient's leukemic blasts also harbored a translocation between chromosomes 11 and 9, resulting in a fusion mutation between MLL and MLLT3 (MLL-MLLT3). As these mutations are characterizes as independent driver mutations, and are each associated with a particularly poor prognosis, the patient's presentation of these mutations placed him in a significantly high-risk group for AML, associated with poor response rates, increased cumulative incidence of relapse, and shortened survival.

This patient was first diagnosed with infantile AML positive for MLL-MLLT3 fusion and treated with standard chemotherapy comprised of cytarabine, daunorubicin and etoposide, achieving a CR. Approximately two years later, the patient relapsed with extramedullary disease (leukemia outside the bone marrow and blood) and was bridged to a stem cell transplant after treatment with salvage chemotherapy comprised of fludarabine, cytarabine, idarubicin, gemtuzumab ozogamicin, and azacytidine. Approximately 6 months after transplant, the patient relapsed again, this time with both the MLL-MLLT3 fusion and a FLT3-A848P mutation. The patient was refractory to an initial cycle of venetoclax plus high dose cytarabine. At this time the patient was provided with crenolanib besylate as part of a compassionate use program. The patient received three days of a liposomal formulation of cytarabine and daunorubicin followed sequentially by 66.7 mg/$m^2$ oral crenolanib besylate three times daily. At the time compassionate use was granted, the patient had 91% bone marrow blasts and extramedullary disease in the liver, spleen, and lymph nodes.

A bone marrow biopsy taken on day 20 of treatment revealed the patient's bone marrow blasts had reduced to less than 5% with full count recovery and the extramedullary disease was cleared, classified as a complete remission. The patient remained on crenolanib monotherapy for an additional month and then received a second bone marrow transplant. The patient remains in alive and in remission more than one year after receiving crenolanib, a significant achievement for a pediatric patient with both FLT3 and MLL fusion mutations with disease that had relapsed post-transplant and was refractory to salvage chemotherapy.

Table 14 below illustrates the ability of crenolanib to clear malignant leukemia in the bone marrow and extramedullary (spleen, liver, and lymph nodes), of Example N, a relapsed/refractory pediatric patient with FLT3-TKD and MLL fusion mutations after treatment with chemotherapy and crenolanib besylate.

| Days on Therapy | Bone Marrow Blast (%) |
|---|---|
| 0 | 91% |
| 20 | <5% |
| 122 | <5% |
| 315 | <5% |

Example O: The effect pf crenolanib besylate therapy in a relapsed/refractory pediatric patient with FLT3-TKD and MLL mutations: achievement of reduction in bone marrow blasts from 60% to 15% and bridge to transplant following crenolanib besylate therapy.

A 9-year-old female was diagnosed with relapsed therapy-related AML positive for FLT3-D835E and FLT3-D835H mutations. The patient's leukemic blasts also harbored a translocation between chromosomes 11 and 19, resulting in a fusion mutation between MLL and ELL (MLL-ELL). As these mutations are characterized as independent driver mutations, and are each associated with a particularly poor prognosis, the patient's presentation of these mutations placed her in a significantly high-risk group for AML, associated with poor response rates, increased cumulative incidence of relapse, and shortened survival.

This patient was originally diagnosed with ALL and achieved complete remission after treatment with standard chemotherapy-based induction, consolidation, and maintenance therapy. After the completion of therapy, the patient was found to have developed therapy-related AML, for which she received a stem cell transplant. Approximately 5 months after transplant, the patient relapsed, and was found to have a translocation between chromosomes 11 and 19, resulting in MLL-ELL fusion, and FLT3-TKD mutations. At this time the patient was given venetoclax and achieved complete remission. Approximately 2 months later, the patient was found to have relapsed, and was provided with 66.7 mg/$m^2$ oral crenolanib besylate three times daily as part of a compassionate use program. At time compassionate use was granted, the patient had 63% bone marrow blasts.

A bone marrow biopsy taken on day 20 of treatment revealed the patient's bone marrow blasts had reduced to 15%, classified as a partial remission. The patient received a second stem cell transplant three months later.

Table 15 below illustrates the ability of crenolanib to clear malignant leukemia in the bone marrow of Example O, a relapsed/refractory pediatric patient with FLT3-TKD and MLL fusion mutations after treatment with chemotherapy and crenolanib besylate.

| Days on Therapy | Bone Marrow Blast (%) |
|---|---|
| 0 | 63% |
| 20 | 15% |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

For each of the claims, each dependent claim can depend both from the independent claim and from each of the prior dependent claims for each and every claim so long as the prior claim provides a proper antecedent basis for a claim term or element.

REFERENCES

Abdel-Wahab, O., Adli, M., LaFave, L. M., Gao, J., Hricik, T., Shih, A. H., . . . Levine, R. L. (2012). ASXL1 mutations promote myeloid transformation through loss of PRC2-mediated gene repression. Cancer Cell, 22(2), 180-193. doi:10.1016/j.ccr.2012.06.032.

Abu-Duhier, F. M., Goodeve, A. C., Wilson, G. A., Gari, M. A., Peake, I. R., Rees, D. C., Reilly, J. T. (2000). FLT3 internal tandem duplication mutations in adult acute myeloid leukaemia define a high-risk group. Br J Haematol, 111(1), 190-195. doi: 10.1046/j.1365-2141.2000.02317.x.

Al Aboud, N., Tupper, C., & Jialal, I. (2021). Genetics, Epigentic Mechanism. In StatPearls [Internet]. Retrieved from https://www.ncbi.nlm.nih.gov/books/NBK532999/.

Amin, H. M., Yang, Y., Shen, Y., Estey, E. H., Giles, F. J., Pierce, S. A., Albitar, M. (2005). Having a higher blast percentage in circulation than bone marrow: clinical implications in myelodysplastic syndrome and acute lymphoid and myeloid leukemias. Leukemia, 19(9), 1567-1572. doi:10.1038/sj.leu.2403876.

Aslanyan, M. G., Kroeze, L. I., Langemeijer, S. M., Koorenhof-Scheele, T. N., Massop, M., van Hoogen, P., Jansen, J. H. (2014). Clinical and biological impact of TET2 mutations and expression in younger adult AML patients treated within the EORTC/GIMEMA AML-12 clinical trial. Ann Hematol, 93(8), 1401-1412. doi: 10.1007/s00277-014-2055-7.

Astolfi, A., Fiore, M., Melchionda, F., Indio, V., Bertuccio, S. N., & Pession, A. (2019). BCOR involvement in cancer. Epigenomics, 11(7), 835-855. doi:10.2217/epi-2018-0195.

Bacher, U., Haferlach, C., Kern, W., Haferlach, T., & Schnittger, S. (2008). Prognostic relevance of FLT3-TKD mutations in AML: the combination matters—an analysis of 3082 patients. Blood, 111(5), 2527-2537. doi:10.1182/blood-2007-05-091215.

Bains, A., Luthra, R., Medeiros, L. J., & Zuo, Z. (2011). FLT3 and NPM1 mutations in myelodysplastic syndromes: Frequency and potential value for predicting progression to acute myeloid leukemia. Am J Clin Pathol, 135(1), 62-69. doi:10.1309/AJCPEI9XU8PYBCIO.

Ball, B. J., Hsu, M., Devlin, S. M., Famulare, C., Cai, S. F., Dunbar, A., Stein, E. M. (2019). RAS Mutations Are Independently Associated with Decreased Overall Survival and Event-Free Survival in Patients with AML Receiving Induction Chemotherapy. Blood, 134(Supplement 1), 18-18. doi:10.1182/blood-2019-125319

Bhamidipati, P. K., Daver, N. G., Kantarjian, H., Pierce, S., Daver, R., Cortes, J. E., Garcia-Manero, G. (2012). FLT3 mutations in myelodysplastic syndromes (MDS) and chronic myelomonocytic leukemia (CMML). Journal of Clinical Oncology, 30(15_suppl), 6597-6597. doi: 10.1200/jco.2012.30.15_suppl.6597.

Bill, M., Mrozek, K., Kohlschmidt, J., Eisfeld, A. K., Walker, C. J., Nicolet, D., Bloomfield, C. D. (2020). Mutational landscape and clinical outcome of patients with de novo acute myeloid leukemia and rearrangements involving 11q23/KMT2A. Proc Natl Acad Sci USA, 117 (42), 26340-26346. doi:10.1073/pnas.2014732117.

Boddu, P., Takahashi, K., Pemmaraju, N., Daver, N., Benton, C. B., Pierce, S., DiNardo, C. D. (2017). Influence of IDH on FLT3-ITD status in newly diagnosed AML. Leukemia, 31(11), 2526-2529. doi:10.1038/leu.2017.244.

Borthakur, G., Kantarjian, H., Ravandi, F., Zhang, W., Konopleva, M., Wright, J. J., Cortes, J. E. (2011). Phase I study of sorafenib in patients with refractory or relapsed acute leukemias. Haematologica, 96(1), 62-68. doi: 10.3324/haematol.2010.030452.

Chen, D., Xia, S., Wang, M., Lin, R., Li, Y., Mao, H., Chen, J. (2019). Mutant and wild-type isocitrate dehydrogenase 1 share enhancing mechanisms involving distinct tyrosine kinase cascades in cancer. Cancer Discov. doi:10.1158/2159-8290.CD-18-1040.

Chen, D., Xia, S., Zhang, R., Li, Y., Famulare, C. A., Fan, H., Chen, J. (2021). Lysine acetylation restricts mutant IDH2 activity to optimize transformation in AML cells. Mol Cell, 81(18), 3833-3847 e3811. doi:10.1016/j.molcel.2021.06.027.

Cheson, B. D., Bennett, J. M., Kopecky, K. J., Buchner, T., Willman, C. L., Estey, E. H., Reporting Standards for Therapeutic Trials in Acute Myeloid, L. (2003). Revised recommendations of the International Working Group for Diagnosis, Standardization of Response Criteria, Treatment Outcomes, and Reporting Standards for Therapeutic Trials in Acute Myeloid Leukemia. J Clin Oncol, 21(24), 4642-4649. doi:10.1200/JCO.2003.04.036.

Chilton, L., Hills, R. K., Burnett, A. K., & Harrison, C. J. (2016). The prognostic significance of trisomy 4 in acute myeloid leukaemia is dependent on age and additional abnormalities. Leukemia, 30(11), 2264-2267. doi: 10.1038/leu.2016.200.

Cho, Y. S., Kim, E. J., Park, U. H., Sin, H. S., & Um, S. J. (2006). Additional sex comb-like 1 (ASXL1), in cooperation with SRC-1, acts as a ligand-dependent coactivator for retinoic acid receptor. J Biol Chem, 281(26), 17588-17598. doi:10.1074/jbc.M512616200.

Choe, S., Wang, H., DiNardo, C. D., Stein, E. M., de Botton, S., Roboz, G. J., Wu, B. (2020). Molecular mechanisms mediating relapse following ivosidenib monotherapy in IDH1-mutant relapsed or refractory AML. Blood Adv, 4(9), 1894-1905. doi:10.1182/bloodadvances.2020001503.

Cortes, J., Foran, J., Ghirdaladze, D., DeVetten, M. P., Zodelava, M., Holman, P., Trikha, M. (2009). AC220, a Potent, Selective, Second Generation FLT3 Receptor Tyrosine Kinase (RTK) Inhibitor, in a First-in-Human (FIH) Phase 1 AML Study. Blood, 114(22), 636-636. Retrieved from http://www.bloodjournal.org/content/114/22/636?sso-checked=true.

Cortes, J., Perl, A., Smith, C., TiborKovacsovics, Herve-Dombret, HartmutDohner, Levis, M. (2011). A Phase II, Open-Label, AC220 Monotherapy Efficacy (ACE) Study in Patients With Acute Myeloid Leukemia (AML) With FLT3-ITD Activating Mutations: Interim Results. Paper presented at the EHA Annual Meeting.

Cristobal, I., Blanco, F. J., Garcia-Orti, L., Marcotegui, N., Vicente, C., Rifon, J., Odero, M. D. (2010). SETBP1 overexpression is a novel leukemogenic mechanism that predicts adverse outcome in elderly patients with acute myeloid leukemia. Blood, 115(3), 615-625. doi:10.1182/blood-2009-06-227363.

Dang, L., White, D. W., Gross, S., Bennett, B. D., Bittinger, M. A., Driggers, E. M., Su, S. M. (2009). Cancer-associated IDH1 mutations produce 2-hydroxyglutarate. Nature, 462(7274), 739-744. doi:10.1038/nature08617

Dohner, H., Estey, E., Grimwade, D., Amadori, S., Appelbaum, F. R., Buchner, T., Bloomfield, C. D. (2017). Diagnosis and management of AML in adults: 2017 ELN recommendations from an international expert panel. Blood, 129(4), 424-447. doi:10.1182/blood-2016-08-733196.

Eckardt, J. N., Stasik, S., Kramer, M., Rollig, C., Kramer, A., Scholl, S., Middeke, J. M. (2021). Loss-of-Function Mutations of BCOR Are an Independent Marker of Adverse Outcomes in Intensively Treated Patients with Acute Myeloid Leukemia. Cancers (Basel), 13(9). doi: 10.3390/cancers13092095.

Ferrone, C. K., Blydt-Hansen, M., & Rauh, M. J. (2020). Age-Associated TET2 Mutations: Common Drivers of Myeloid Dysfunction, Cancer and Cardiovascular Disease. Int J Mol Sci, 21(2). doi:10.3390/ijms21020626.

Gelsi-Boyer, V., Brecqueville, M., Devillier, R., Murati, A., Mozziconacci, M. J., & Birnbaum, D. (2012). Mutations in ASXL1 are associated with poor prognosis across the spectrum of malignant myeloid diseases. J Hematol Oncol, 5, 12. doi:10.1186/1756-8722-5-12.

Gilliland, D. G., & Griffin, J. D. (2002). The roles of FLT3 in hematopoiesis and leukemia. Blood, 100(5), 1532-1542. doi:10.1182/blood-2002-02-0492

Griswold, I. J., Shen, L. J., La Rosee, P., Demehri, S., Heinrich, M. C., Braziel, R. M., Deininger, M. W. (2004). Effects of MLN518, a dual FLT3 and KIT inhibitor, on normal and malignant hematopoiesis. Blood, 104(9), 2912-2918. doi:10.1182/blood-2003-05-1669.

Herold, T., Metzeler, K. H., Vosberg, S., Hartmann, L., Rollig, C., Stolzel, F., Greif, P. A. (2014). Isolated trisomy 13 defines a homogeneous AML subgroup with high frequency of mutations in spliceosome genes and poor prognosis. Blood, 124(8), 1304-1311. doi:10.1182/blood-2013-12-540716.

Hou, H. A., Kuo, Y. Y., Tang, J. L., Chou, W. C., Yao, M., Lai, Y. J., Tien, H. F. (2014). Clinical implications of the SETBP1 mutation in patients with primary myelodysplastic syndrome and its stability during disease progression. Am J Hematol, 89(2), 181-186. doi:10.1002/ajh.23611.

Hou, H. A., Liu, C. Y., Kuo, Y. Y., Chou, W. C., Tsai, C. H., Lin, C. C., Tien, H. F. (2016). Splicing factor mutations predict poor prognosis in patients with de novo acute myeloid leukemia. Oncotarget, 7(8), 9084-9101. doi: 10.18632/oncotarget.7000

Kaner, J. D., Mencia-Trinchant, N., Schaap, A., Roboz, G. J., Lee, S., Desai, P., Ritchie, E. K. (2018). Acute Myeloid Leukemia (AML) with Somatic Mutations in PTPN11 Is Associated with Treatment Resistance and Poor Overall Survival. Blood, 132(Supplement 1), 2760-2760. doi: 10.1182/blood-2018-99-110319.

Kelly, M. J., So, J., Rogers, A. J., Gregory, G., Li, J., Zethoven, M., Kats, L. M. (2019). Bcor loss perturbs myeloid differentiation and promotes leukaemogenesis. Nat Commun, 10(1), 1347. doi:10.1038/s41467-019-09250-6.

Kindler, T., Lipka, D. B., & Fischer, T. (2010). FLT3 as a therapeutic target in AML: still challenging after all these years. Blood, 116(24), 5089-5102. doi:10.1182/blood-2010-04-261867.

Kiyoi, H., Naoe, T., Nakano, Y., Yokota, S., Minami, S., Miyawaki, S., Ueda, R. (1999). Prognostic implication of FLT3 and N-RAS gene mutations in acute myeloid leukemia. Blood, 93(9), 3074-3080. Retrieved from https://www.ncbi.nlm.nih.gov/pubmed/10216104.

Kiyoi, H., Naoe, T., Yokota, S., Nakao, M., Minami, S., Kuriyama, K., Ohno, R. (1997). Internal tandem duplication of FLT3 associated with leukocytosis in acute promyelocytic leukemia. Leukemia Study Group of the Ministry of Health and Welfare (Kohseisho). Leukemia, 11(9), 1447-1452. doi:10.1038/sj.leu.2400756.

Kiyoi, H., Towatari, M., Yokota, S., Hamaguchi, M., Ohno, R., Saito, H., & Naoe, T. (1998). Internal tandem duplication of the FLT3 gene is a novel modality of elongation mutation which causes constitutive activation of the product. Leukemia, 12(9), 1333-1337. Retrieved from https://www.ncbi.nlm.nih.gov/pubmed/9737679.

Kottaridis, P. D., Gale, R. E., Frew, M. E., Harrison, G., Langabeer, S. E., Belton, A. A., Linch, D. C. (2001). The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials. Blood, 98(6), 1752-1759. doi:10.1182/blood.V98.6.1752.

Levis, M., Allebach, J., Tse, K. F., Zheng, R., Baldwin, B. R., Smith, B. D., Small, D. (2002). A FLT3-targeted tyrosine kinase inhibitor is cytotoxic to leukemia cells in vitro and in vivo. Blood, 99(11), 3885-3891. Retrieved from https://www.ncbi.nlm.nih.gov/pubmed/12010785.

Levis, M., & Small, D. (2004). Small molecule FLT3 tyrosine kinase inhibitors. Curr Pharm Des, 10(11), 1183-1193. doi:10.2174/1381612043452604.

Lewis, N. L., Lewis, L. D., Eder, J. P., Reddy, N. J., Guo, F., Pierce, K. J., Cohen, R. B. (2009). Phase I study of the safety, tolerability, and pharmacokinetics of oral CP-868, 596, a highly specific platelet-derived growth factor receptor tyrosine kinase inhibitor in patients with advanced cancers. J Clin Oncol, 27(31), 5262-5269. doi: 10.1200/JCO.2009.21.8487.

Mendler, J. H., Maharry, K., Radmacher, M. D., Mrozek, K., Becker, H., Metzeler, K. H., . . . Bloomfield, C. D. (2012). RUNX1 mutations are associated with poor outcome in younger and older patients with cytogenetically normal acute myeloid leukemia and with distinct gene and MicroRNA expression signatures. J Clin Oncol, 30(25), 3109-3118. doi:10.1200/JCO.2011.40.6652.

Meyer, C., Hofmann, J., Burmeister, T., Groger, D., Park, T. S., Emerenciano, M., Marschalek, R. (2013). The MLL recombinome of acute leukemias in 2013. Leukemia, 27(11), 2165-2176. doi:10.1038/leu.2013.135.

Meyer, C., Kowarz, E., Hofmann, J., Renneville, A., Zuna, J., Trka, J., Marschalek, R. (2009). New insights to the MLL recombinome of acute leukemias. Leukemia, 23(8), 1490-1499. doi:10.1038/leu.2009.33.

Murata, K., Kumagai, H., Kawashima, T., Tamitsu, K., Irie, M., Nakajima, H., Kitamura, T. (2003). Selective cytotoxic mechanism of GTP-14564, a novel tyrosine kinase inhibitor in leukemia cells expressing a constitutively active Fms-like tyrosine kinase 3 (FLT3). J Biol Chem, 278(35), 32892-32898. doi:10.1074/jbc.M210405200.

Nguyen, N., Vishwakarma, B. A., Oakley, K., Han, Y., Przychodzen, B., Maciejewski, J. P., & Du, Y. (2016). Myb expression is critical for myeloid leukemia development induced by Setbp1 activation. Oncotarget, 7(52), 86300-86312. doi:10.18632/oncotarget.13383.

O'Farrell, A. M., Abrams, T. J., Yuen, H. A., Ngai, T. J., Louie, S. G., Yee, K. W., Cherrington, J. M. (2003). SU11248 is a novel FLT3 tyrosine kinase inhibitor with potent activity in vitro and in vivo. Blood, 101(9), 3597-3605. doi:10.1182/blood-2002-07-2307.

Papaemmanuil, E., Gerstung, M., Bullinger, L., Gaidzik, V. I., Paschka, P., Roberts, N. D., Campbell, P. J. (2016). Genomic Classification and Prognosis in Acute Myeloid Leukemia. N Engl J Med, 374(23), 2209-2221. doi: 10.1056/NEJMoa1516192.

Paschka, P., Marcucci, G., Ruppert, A. S., Whitman, S. P., Mrozek, K., Maharry, K., Bloomfield, C. D. (2008). Wilms' tumor 1 gene mutations independently predict poor outcome in adults with cytogenetically normal acute myeloid leukemia: a cancer and leukemia group B study. J Clin Oncol, 26(28), 4595-4602. doi:10.1200/JCO.2007.15.2058.

Piazza, R., Magistroni, V., Redaelli, S., Mauri, M., Massimino, L., Sessa, A., Gambacorti-Passerini, C. (2018). SETBP1 induces transcription of a network of development genes by acting as an epigenetic hub. Nat Commun, 9(1), 2192. doi:10.1038/s41467-018-04462-8.

Pratcorona, M., Abbas, S., Sanders, M. A., Koenders, J. E., Kavelaars, F. G., Erpelinck-Verschueren, C. A., Valk, P. J. (2012). Acquired mutations in ASXL1 in acute myeloid leukemia: prevalence and prognostic value. Haematologica, 97(3), 388-392. doi:10.3324/haematol.2011.051532.

Quivoron, C., Couronne, L., Della Valle, V., Lopez, C. K., Plo, I., Wagner-Ballon, O., . . . Bernard, O. A. (2011). TET2 inactivation results in pleiotropic hematopoietic abnormalities in mouse and is a recurrent event during human lymphomagenesis. Cancer Cell, 20(1), 25-38. doi: 10.1016/j.ccr.2011.06.003.

Rasmussen, K. D., & Helin, K. (2016). Role of TET enzymes in DNA methylation, development, and cancer. Genes Dev, 30(7), 733-750. doi:10.1101/gad.276568.115

Sasaki, M., Knobbe, C. B., Munger, J. C., Lind, E. F., Brenner, D., Brustle, A., Mak, T. W. (2012). IDH1 (R132H) mutation increases murine haematopoietic progenitors and alters epigenetics. Nature, 488(7413), 656-659. doi:10.1038/nature11323.

Schnittger, S., Schoch, C., Dugas, M., Kern, W., Staib, P., Wuchter, C., Hiddemann, W. (2002). Analysis of FLT3 length mutations in 1003 patients with acute myeloid leukemia: correlation to cytogenetics, FAB subtype, and prognosis in the AMLCG study and usefulness as a marker for the detection of minimal residual disease. Blood, 100(1), 59-66. Retrieved from https://www.ncbi.nlm.nih.gov/pubmed/12070009.

Small, D. (2006). FLT3 mutations: biology and treatment. Hematology Am Soc Hematol Educ Program, 178-184. doi:10.1182/asheducation-2006.1.178.

Smith, B. D., Levis, M., Beran, M., Giles, F., Kantarjian, H., Berg, K., Small, D. (2004). Single-agent CEP-701, a novel FLT3 inhibitor, shows biologic and clinical activity in patients with relapsed or refractory acute myeloid leukemia. Blood, 103(10), 3669-3676. doi:10.1182/blood-2003-11-3775.

Stirewalt, D. L., & Radich, J. P. (2003). The role of FLT3 in haematopoietic malignancies. Nat Rev Cancer, 3(9), 650-665. doi:10.1038/nrc1169.

Stone, R. M., DeAngelo, D. J., Klimek, V., Galinsky, I., Estey, E., Nimer, S. D., Griffin, J. D. (2005). Patients with acute myeloid leukemia and an activating mutation in FLT3 respond to a small-molecule FLT3 tyrosine kinase inhibitor, PKC412. Blood, 105(1), 54-60. doi:10.1182/blood-2004-03-0891.

Sun, Y., Chen, B. R., & Deshpande, A. (2018). Epigenetic Regulators in the Development, Maintenance, and Therapeutic Targeting of Acute Myeloid Leukemia. Front Oncol, 8, 41. doi:10.3389/fonc.2018.00041.

Thiede, C., Steudel, C., Mohr, B., Schaich, M., Schakel, U., Platzbecker, U., Illmer, T. (2002). Analysis of FLT3-activating mutations in 979 patients with acute myelogenous leukemia: association with FAB subtypes and identification of subgroups with poor prognosis. Presented in part at the 42nd Annual Meeting of the American Society of Hematology, Dec. 1-5, 2000, San Francisco, Calif. (abstract 2334). 99(12), 4326-4335. doi:10.1182/blood.V99.12.4326.

Thol, F., Suchanek, K. J., Koenecke, C., Stadler, M., Platzbecker, U., Thiede, C., Heuser, M. (2013). SETBP1 mutation analysis in 944 patients with MDS and AML. Leukemia, 27(10), 2072-2075. doi:10.1038/leu.2013.145

Tse, K. F., Novelli, E., Civin, C. I., Bohmer, F. D., & Small, D. (2001). Inhibition of FLT3-mediated transformation by use of a tyrosine kinase inhibitor. Leukemia, 15(7), 1001-1010. doi:10.1038/sj.leu.2402199.

Tyner, J. W., Tognon, C. E., Bottomly, D., Wilmot, B., Kurtz, S. E., Savage, S. L., Druker, B. J. (2018). Functional genomic landscape of acute myeloid leukaemia. Nature. doi:10.1038/s41586-018-0623-z.

VanderWalde, A., & Vora, N. L. (2016). Genetics of Acute Myeloid Leukemia. Medscape Drugs, Diseases & Procedures. Retrieved from http://emedicine.medscape.com/article/1936033-overview.

Venney, D., Mohd-Sarip, A., & Mills, K. I. (2021). The Impact of Epigenetic Modifications in Myeloid Malignancies. Int J Mol Sci, 22(9). doi:10.3390/ijms22095013

Winters, A. C., & Bernt, K. M. (2017). MLL-Rearranged Leukemias—An Update on Science and Clinical Approaches. Front Pediatr, 5, 4. doi:10.3389/fped.2017.00004

Yamamoto, Y., Kiyoi, H., Nakano, Y., Suzuki, R., Kodera, Y., Miyawaki, S., Naoe, T. (2001). Activating mutation of D835 within the activation loop of FLT3 in human hematologic malignancies. Blood, 97(8), 2434-2439. Retrieved from https://www.ncbi.nlm.nih.gov/pubmed/11290608.

Yee, K. W., O'Farrell, A. M., Smolich, B. D., Cherrington, J. M., McMahon, G., Wait, C. L., Heinrich, M. C. (2002). SU5416 and SU5614 inhibit kinase activity of wild-type and mutant FLT3 receptor tyrosine kinase. Blood, 100(8), 2941-2949. doi:10.1182/blood-2002-02-0531.

Yu, J., Li, Y., Zhang, D., Wan, D., & Jiang, Z. (2020). Clinical implications of recurrent gene mutations in acute myeloid leukemia. Experimental Hematology & Oncology, 9(1), 4. doi:10.1186/s40164-020-00161-7.

Zhang, A., Liu, Y., Wei, S., Gong, B., Zhou, C., Wang, Y., Wang, J. (2020). BCOR Mutations in Acute Myeloid Leukemia: Clonal Evolution and Prognosis. Blood, 136 (Supplement 1), 4-4. doi:10.1182/blood-2020-137127.

Zorko, N. A., Bernot, K. M., Whitman, S. P., Siebenaler, R. F., Ahmed, E. H., Marcucci, G. G., Caligiuri, M. A. (2012). Mll partial tandem duplication and Flt3 internal tandem duplication in a double knock-in mouse recapitulates features of counterpart human acute myeloid leukemias. Blood, 120(5), 1130-1136. doi:10.1182/blood-2012-03-415067.

What is claimed is:

1. A method for treating a human patient with Crenolanib, wherein the human patient is suffering from a FLT3 mutated leukemia, the method comprising:

a) obtaining or having obtained a leukemia biological sample from the human patient;

b) performing or having performed a genotyping assay on the biological sample to determine that the human patient has both a mutated FLT3 or a constitutively active FLT3 mutant and one or more driver mutations in a TET2 epigenetic regulator gene that result in a loss-of-function mutation of a TET2 protein;

c) determining that the human patient has a poor prognosis for the FLT3 mutated leukemia based on detecting the presence of both the mutated FLT3 and the one or more driver mutations in TET2 in the sample; and d) administering to the patient determined to have the poor prognosis a therapeutically effective amount of Crenolanib or a pharmaceutically acceptable salt thereof, to treat the leukemia.

2. The method of claim 1, wherein the FLT3 mutation is selected from at least one of FLT3-ITD or FLT3-TKD.

3. The method of claim 1, wherein the therapeutically effective amount of Crenolanib or the pharmaceutically acceptable salt thereof are from about 50 to 500 mg per day, 100 to 450 mg per day, 200 to 400 mg per day, 300 to 500 mg per day, 350 to 500 mg per day, or 400 to 500 mg per day.

4. The method of claim 1, wherein the Crenolanib or the pharmaceutically acceptable salt thereof is Crenolanib besylate, Crenolanib phosphate, Crenolanib lactate, Crenolanib hydrochloride, Crenolanib citrate, Crenolanib acetate, Crenolanib toluenesulphonate, and Crenolanib succinate.

5. A method for treating a human patient suffering from acute myelogenous leukemia (AML) comprising:

a) obtaining a biological sample from the human patient;

b) determining from the sample that the human patient has AML with a deregulated FLT3 receptor or a constitutively active FLT3 receptor;

c) determining from the sample that the human patient has one or more driver mutations in epigenetic regulator protein TET2 that result in a loss-of-function mutation of TET2;

d) determining that the human patient has a poor prognosis for AML based on determining the presence of both the mutated FLT3 and the one or more driver mutations in TET2 in the sample; and e) administering to the patient determined to have the poor prognosis a therapeutically effective amount of Crenolanib or a pharmaceutically acceptable salt thereof, thereby treating the AML.

6. A method for specifically inhibiting a deregulated or constitutively active FLT3 receptor tyrosine kinase, comprising:

a) obtaining a sample from a human patient having acute myelogenous leukemia (AML);

b) determining that the AML has a FLT3 receptor tyrosine kinase that is deregulated or constitutively active and one or more driver mutations in TET2 that result in a loss-of-function mutation of TET2 by performing or having performed genetic testing on the sample from the patient;

c) determining that the human patient has a poor prognosis based on determining that the AML has both the deregulated or constitutively active FLT3 receptor tyrosine kinase and the one or more driver mutations in TET2; and d) administering a therapeutically effective amount of Crenolanib or a salt thereof, sufficient to eliminate the AML, to the human patient determined to have both the deregulated or constitutively active FLT3 receptor tyrosine kinase and the one or more driver mutations in TET2.

7. The method of claim 1, wherein the therapeutically effective amount of Crenolanib or the pharmaceutically acceptable salt thereof is administered at least one of continuously, intermittently, systemically, or locally.

8. The method of claim 1, wherein the therapeutically effective amount of Crenolanib or the pharmaceutically acceptable salt thereof is administered orally, intravenously, or intraperitoneally.

9. The method of claim 1, wherein the therapeutically effective amount of Crenolanib is administered up to three times or more a day for as long as the human patient is in need of treatment for the leukemia.

10. The method of claim 1, wherein the therapeutically effective amount of Crenolanib is provided at least one of sequentially or concomitantly, with another pharmaceutical agent in a newly diagnosed human leukemia patient, to maintain remission of an existing human leukemia patient, or in a relapsed/refractory human leukemia patient.

11. The method of claim 1, wherein the therapeutically effective amount of Crenolanib is provided as a single agent or in combination with another pharmaceutical agent in a patient with a newly diagnosed leukemia, to maintain remission, or in a relapse/refractory human leukemia patient.

12. The method of claim 1, wherein the therapeutically effective amount of Crenolanib is provided as a single agent or in combination with another pharmaceutical agent in a newly diagnosed human pediatric leukemia patient, to maintain remission, or in a relapsed/refractory human pediatric leukemia patient.

13. The method of claim 1, wherein the therapeutically effective amount of Crenolanib is provided to a human patient relapsed/refractory to another tyrosine kinase inhibitor or chemotherapy.

14. The method of claim 5, wherein the FLT3 mutation is selected from at least one of FLT3-ITD or FLT3-TKD.

15. The method of claim 5, wherein:

the therapeutically effective amount of Crenolanib or the pharmaceutically acceptable salt thereof are from about 50 to 500 mg per day, 100 to 450 mg per day, 200 to 400 mg per day, 300 to 500 mg per day, 350 to 500 mg per day, or 400 to 500 mg per day;

the therapeutically effective amount of Crenolanib or the pharmaceutically acceptable salt thereof is administered at least one of continuously, intermittently, systemically, or locally;

the therapeutically effective amount of Crenolanib or the pharmaceutically acceptable salt thereof is administered orally, intravenously, or intraperitoneally;

the therapeutically effective amount of Crenolanib is administered up to three times or more a day for as long as the human patient is in need of treatment for the leukemia;

the therapeutically effective amount of Crenolanib is provided at least one of sequentially or concomitantly, with another pharmaceutical agent in a newly diagnosed human leukemia patient, to maintain remission of an existing human leukemia patient, or in a relapsed/refractory human leukemia patient;

the therapeutically effective amount of Crenolanib is provided as a single agent or in combination with another pharmaceutical agent in a patient with a newly diagnosed leukemia, to maintain remission, or in a relapse/refractory human leukemia patient;

the therapeutically effective amount of Crenolanib is provided as a single agent or in combination with another pharmaceutical agent in a newly diagnosed human pediatric leukemia patient, to maintain remission, or in a relapsed/refractory human pediatric leukemia patient; or the therapeutically effective amount of Crenolanib is provided to a human patient relapsed/refractory to another tyrosine kinase inhibitor or chemotherapy.

16. The method of claim 5, wherein the Crenolanib or the pharmaceutically acceptable salt thereof is Crenolanib besylate, Crenolanib phosphate, Crenolanib lactate, Crenolanib hydrochloride, Crenolanib citrate, Crenolanib acetate, Crenolanib toluenesulphonate, and Crenolanib succinate.

17. The method of claim 6, wherein the FLT3 mutation is selected from at least one of FLT3-ITD or FLT3-TKD.

18. The method of claim 6, wherein:

the therapeutically effective amount of Crenolanib or the pharmaceutically acceptable salt thereof are from about 50 to 500 mg per day, 100 to 450 mg per day, 200 to 400 mg per day, 300 to 500 mg per day, 350 to 500 mg per day, or 400 to 500 mg per day;

the therapeutically effective amount of Crenolanib or the pharmaceutically acceptable salt thereof is administered at least one of continuously, intermittently, systemically, or locally;

the therapeutically effective amount of Crenolanib or the pharmaceutically acceptable salt thereof is administered orally, intravenously, or intraperitoneally;

the therapeutically effective amount of Crenolanib is administered up to three times or more a day for as long as the human patient is in need of treatment for the leukemia;

the therapeutically effective amount of Crenolanib is provided at least one of sequentially or concomitantly, with another pharmaceutical agent in a newly diagnosed human leukemia patient, to maintain remission of an existing human leukemia patient, or in a relapsed/refractory human leukemia patient;

the therapeutically effective amount of Crenolanib is provided as a single agent or in combination with another pharmaceutical agent in a patient with a newly diagnosed leukemia, to maintain remission, or in a relapse/refractory human leukemia patient;

the therapeutically effective amount of Crenolanib is provided as a single agent or in combination with another pharmaceutical agent in a newly diagnosed human pediatric leukemia patient, to maintain remission, or in a relapsed/refractory human pediatric leukemia patient; or the therapeutically effective amount of Crenolanib is provided to a human patient relapsed/refractory to another tyrosine kinase inhibitor or chemotherapy.

19. The method of claim 6, wherein the Crenolanib or the pharmaceutically acceptable salt thereof is Crenolanib besylate, Crenolanib phosphate, Crenolanib lactate, Crenolanib hydrochloride, Crenolanib citrate, Crenolanib acetate, Crenolanib toluenesulphonate, and Crenolanib succinate.

* * * * *